US009745587B2

(12) United States Patent
Gilmore et al.

(10) Patent No.: US 9,745,587 B2
(45) Date of Patent: Aug. 29, 2017

(54) NUCLEIC ACID CONSTRUCTS CONTAINING ORTHOGONAL SITE SELECTIVE RECOMBINASES (OSSRS)

(75) Inventors: Joshua M. Gilmore, Emeryville, CA (US); J. Christopher Anderson, San Francisco, CA (US); John E. Dueber, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/088,288

(22) Filed: Apr. 15, 2011

(65) Prior Publication Data

US 2012/0135524 A1 May 31, 2012

Related U.S. Application Data

(63) Continuation-in-part of application No. PCT/US2009/060275, filed on Oct. 9, 2009.

(60) Provisional application No. 61/104,239, filed on Oct. 9, 2008.

(51) Int. Cl.
*C12N 15/63* (2006.01)
*C12N 15/10* (2006.01)
*C12N 15/82* (2006.01)

(52) U.S. Cl.
CPC .............. *C12N 15/63* (2013.01); *C12N 15/10* (2013.01); *C12N 15/8213* (2013.01)

(58) Field of Classification Search
None
See application file for complete search history.

(56) References Cited

U.S. PATENT DOCUMENTS

| | | | | |
|---|---|---|---|---|
| 2003/0022375 | A1* | 1/2003 | Itoh et al. | 435/455 |
| 2006/0073593 | A1* | 4/2006 | Byrd et al. | 435/455 |
| 2006/0078902 | A1* | 4/2006 | Bunting | C12N 15/111 435/6.11 |

* cited by examiner

*Primary Examiner* — Catherine S Hibbert
(74) *Attorney, Agent, or Firm* — Robin C. Chiang; Lawrence Berkeley National Laboratory

(57) ABSTRACT

The present invention provides for a recombinant nucleic acid comprising a nucleotide sequence comprising a plurality of constructs, wherein each construct independently comprises a nucleotide sequence of interest flanked by a pair of recombinase recognition sequences. Each pair of recombinase recognition sequences is recognized by a distinct recombinase. Optionally, each construct can, independently, further comprise one or more genes encoding a recombinase capable of recognizing the pair of recombinase recognition sequences of the construct. The recombinase can be an orthogonal (non-cross reacting), site-selective recombinase (OSSR).

10 Claims, 8 Drawing Sheets

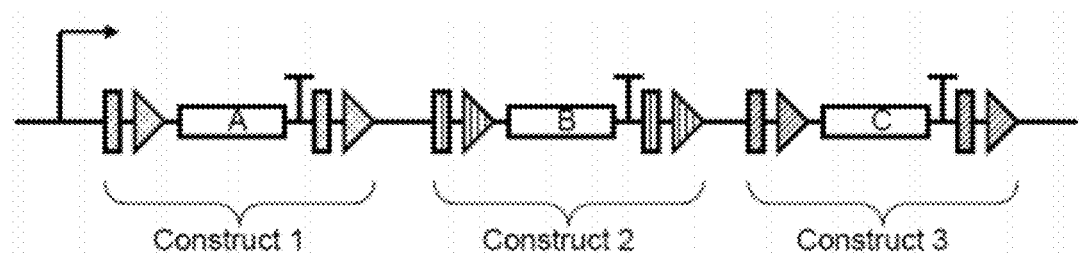
Figure 1
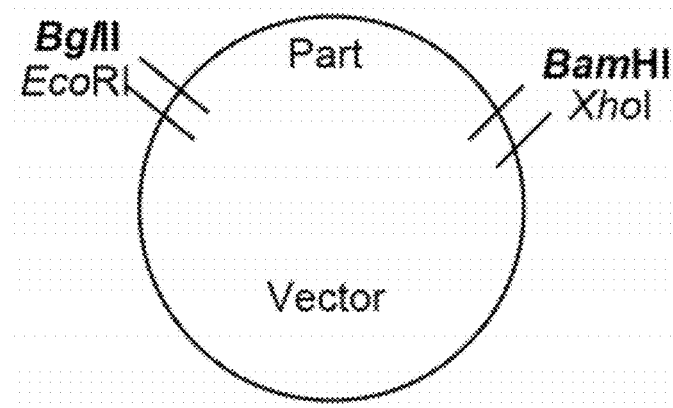
Figure 2
GAATTCaaaAGATCTPARTSEQUENCE1GGATCCaaaCTCGAG
AGATCTPARTSEQUENCE1GGATCC
　　　　　　　　　　　　　AGATCTPARTSEQUENCE2GGATCC
　　　　　　　　　　　GlySer
AGATCTPARTSEQUENCE1GGATCCPARTSEQUENCE2GGATCC
Figure 3
AGATCTATG_MIDDLE_OF_PART_TAAGGATCC
AGATCTGTG_MIDDLE_OF_PART_TGAGGATCC
Figure 4

Type II    AGATCTATGAAATTTCCCGGGAAATTTGGATCC

Type III   AGATCTCATCATCATCATCATCATTAAGGATCC

Type IV    AGATCTAAATTTCCCGGGAAATTTCCCGGATCC

Figure 5

AGATCTGAAAGAGGAGAAAGGATCC

AGATCTATG_ORF_Part_TAAGGATCC

.RBS.
AGATCTGAAAGAGGAGAAAGGATCCATG_ORF_Part_TAAGGATCC

Figure 6

AGATCTTCC_Middle_of_Ptet_TAGAGATACTGAGCACGGATCC

Figure 7

...CUUUCUGCGUUUAUA3'

AGATCTCCA_Middle_of_Ptet_CTTTCTGCGTTTATAGGATCC

Figure 8

NUCLEIC ACID CONSTRUCTS CONTAINING ORTHOGONAL SITE SELECTIVE RECOMBINASES (OSSRS)

CROSS-REFERENCE TO RELATED APPLICATIONS

This application claims priority as a continuation-in-part application of PCT International Patent Application No. PCT/US2009/060275, filed Oct. 9, 2009, which claims priority to U.S. Provisional Patent Application Ser. No. 61/104,239, filed on Oct. 9, 2008; which are hereby incorporated by reference.

STATEMENT OF GOVERNMENTAL SUPPORT

The invention described and claimed herein was made in part utilizing funds supplied by the U.S. Department of Energy under Contract No. DE-AC02-05CH11231. The government has certain rights in this invention.

FIELD OF THE INVENTION

This invention relates generally to the use of recombinases.

BACKGROUND OF THE INVENTION

Phage recombinases are splicing enzymes used by virions to insert or remove their genomic DNA from a host chromosome. The use of recombinases (or integrases) for genomic manipulation is well established. Site-specific recombinases are significant tools in a variety of applications in research, medicine, and biotechnology. Conditional gene targeting using site-specific recombinases has enabled the functional analysis of genes, which cannot be inactivated in the germline. Site-specific recombinases also allow the precise integration of open reading frames (ORFs) encoding proteins of interest into highly active gene loci in cell lines and transgenic animals. Recombinases are disclosed in the following references: Groth, Amy C.; Calos, Michele P. *J. Mol. Biol* (2004) 335, 667-678; Silver, Daniel P.; Livingston, David M. *Molecular Cell* (2001), 8, 233-243; Sauer, Brian; McDermott, Jeffrey. *Nucleic Acids Research* (2004) 32(20), 6086-6095; Yagil, Ezra; Dorgai, László; Weisberg, Robert A. *J. Mol. Biol* (1995) 252, 163-177; and, Dorgai, László; Yagil, Ezra; Weisberg, Robert A. *J. Mol. Biol* (1995) 252, 178-188.

SUMMARY OF THE INVENTION

The present invention provides for a recombinant nucleic acid comprising a nucleotide sequence comprising a plurality of constructs, wherein each construct independently comprises a nucleotide sequence of interest flanked by a pair of recombinase recognition sequences. Each pair of recombinase recognition sequences is recognized by a distinct recombinase. Optionally, each construct can, independently, further comprise one or more genes encoding a recombinase capable of recognizing the pair of recombinase recognition sequences of the construct.

The present invention provides for a recombinant nucleic acid comprising a first construct and a second construct; wherein the first construct comprises a nucleotide sequence encoding a first recognition sequence of a first recombinase, a second recognition sequence of the first recombinase, and a first nucleotide sequence of interest located between the first and second recognition sequence of the first recombinase; wherein the second construct comprises a nucleotide sequence encoding a first recognition sequence of a second recombinase, a second recognition sequence of the second recombinase, and a second nucleotide sequence of interest located between the first and second recognition sequence of the second recombinase; wherein the second construct is located downstream of the first construct; wherein the first recombinase and the second recombinase do not cross react with the recognition sequence of the other.

A recombinase that can be used in the present invention is an orthogonal (non-cross reacting), site-selective recombinase (OSSR). An OSSR is a recombinase that recognizes a specific recognition site or nucleotide sequence and does not cross-react with the recognition site or nucleotide sequence of another recombinase.

The present invention also provides for a recombinant vector comprising the recombinant nucleic acid. The present invention also provides for a vector or expression vector comprising a recombinant nucleic acid of the present invention.

The present invention further provides for a host cell comprising any of the recombinant nucleic acid or vector of the present invention. In some embodiments, the recombinant nucleic acid is integrated into a chromosome or replicon of the host cell. The host cell can be an eukaryotic or a prokaryotic cell.

The present invention further provides for a host organism comprising one or more host cells of the present invention. In some embodiments, all of the cells of the host organism comprise a recombinant nucleic acid of the present invention.

The present invention provides for a method of excising or deleting one or more nucleotide sequence of interest from a host cell, comprising: (a) providing a signal to a host cell to activate expression from a promoter in the host cell, wherein the host cell comprises a promoter upstream of a plurality of constructs, wherein each construct independently comprises a nucleotide sequence of interest flanked by a pair of recombinase recognition sequences; and (b) excising or deleting one or more nucleotide sequence of interest.

The present invention provides for a method of excising or deleting a first nucleotide sequence of interest from a host cell, comprising: (a) providing a signal to a host cell to activate expression from a promoter in the host cell, wherein the host cell comprises a promoter upstream of a first construct and a second construct; and (b) excising or deleting a first nucleotide sequence of interest; wherein the first construct comprises a nucleotide sequence encoding a first recognition sequence of a first recombinase, a second recognition sequence of the first recombinase, and the first nucleotide sequence of interest located between the first and second recognition sequence of the first recombinase; wherein the second construct comprises a nucleotide sequence encoding a first recognition sequence of a second recombinase, a second recognition sequence of the second recombinase, and a second nucleotide sequence of interest located between the first and second recognition sequence of the second recombinase; wherein the second construct is located downstream of the first construct; wherein the first recombinase and the second recombinase do not cross react with the recognition sequence of the other.

The present invention further provides for a system capable of noise canceling with non-coding interfering RNA suppression.

The present invention further provides for a system capable of noise canceling with dominant negative complexation.

The present invention further provides for a system comprising a switch that is controlled by the relative expression of two variable promoters

BRIEF DESCRIPTION OF THE DRAWINGS

The foregoing aspects and others will be readily appreciated by the skilled artisan from the following description of illustrative embodiments when read in conjunction with the accompanying drawings.

FIG. 1 shows an illustration of an exemplary recombinant nucleic acid of the present invention. Three representative constructs are shown. Each horizontal bar represents a separate ORF of interest. Each vertical bar represents a recombinase gene and the triangles with the same hatch marks indicate its corresponding recognition sites. In all figures, each "T" represents a transcription terminator element. In all figures, each L-shaped line with an arrow represents a promoter.

FIG. 2 shows an exemplary Potter Standard Plasmid. The name of such a plasmid is the form of "Vector-Part". For example, a "Part" is defined as the sequence between BglII and BamHI sites. For example, a "Vector" is defined as the sequence between BamHI and BglII sites. As such, the "Vector" can be defined as a special part containing EcoRI and XhoI restriction sites. Any number of "Parts" and "Vectors" can be individually defined as basic parts or composite parts.

FIG. 3 shows an exemplary standard assembly. The nucleotide sequences from top to bottom are SEQ ID NOs:4-7, respectively.

FIG. 4 shows an exemplary Type I coding sequences, wherein the start and stop codons are placed directly adjacent to the BglII and BamHI sites, respectively. The start codons can be ATG, CTG, TTG, or GTG. The top nucleotide sequence is SEQ ID NO:8, and the bottom nucleotide sequence is SEQ ID NO:9.

FIG. 5 shows exemplary Type II-Type IV coding sequences (SEQ ID NOs:10-12, respectively). The coding sequences allow the construction of ORF fusions for chimeric and tagged proteins. GlySer scars separate junctions between fused peptides.

FIG. 6 shows an exemplary Ribosome Binding Site (RBS), and the spacing of a ribosome binding site relative to the start codon is fixed. Shown is a (likely) strong RBS. The nucleotide sequences from top to bottom are SEQ ID NOs:13-15, respectively.

FIG. 7 shows an exemplary promoter (SEQ ID NO:16). The transcriptional start site (+1) is located at the position directly 5' to the BamHI site (whenever possible).

FIG. 8 shows an exemplary terminator. The transcriptional termination site is located at the position directly 5' to the BamHI site (whenever possible). The top nucleotide sequence is SEQ ID NO:17, and the bottom nucleotide sequence is SEQ ID NO:18.

DETAILED DESCRIPTION

Figure 9:
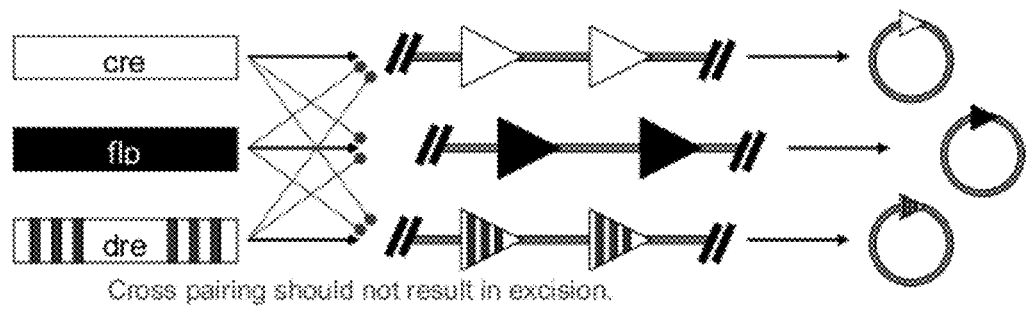
FIG. 9 shows an example of cross pairing (of three different recombinases) which should not result in excision.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a sequence" includes a plurality of such sequences, and so forth.

These and other objects, advantages, and features of the invention will become apparent to those persons skilled in the art upon reading the details of the invention as more fully described below.

In some embodiments, the recombinant nucleic acid comprises two or more constructs, three or more constructs, four or more constructs, five or more constructs, or ten or more constructs. In some embodiments, the recombinant nucleic acid comprises up to ten constructs.

In some embodiments, the recombinant nucleic acid further comprises a third construct comprising a nucleotide sequence encoding a first recognition sequence of a third recombinase, a second recognition sequence of the third recombinase, and a third nucleotide sequence of interest located between the first and second recognition sequence of the third recombinase. In some embodiment, the recombinant nucleic acid further comprises a fourth, fifth, or/and etc. construct(s), each construct comprising a nucleotide sequence encoding a first recognition sequence of a unique recombinase, a second recognition sequence of the unique recombinase, and a nucleotide sequence of interest located between the first and second recognition sequence of the unique recombinase, wherein the unique recombinase is a recombinase is distinct of any of the other recombinase which recognizes a recognition sequence within the recombinant nucleic acid.

See FIG. 1 for one embodiment of the invention.

The use of recombinases for manipulation of genomic sequences is well known to those skilled in the art. Commonly, the recombinase is used as follows: a target DNA containing a selection marker is initially inserted into a chromosome at a desired location. Following selection, an OSSR is used to extract the selection marker. In this method, the toolkit of two recombinases and one selection marker can be used repeatedly to significantly modify the organism under study. The orthogonality of the recombinase is important to prevent destructive or unpredictable recombination events.

A recombinase that can be used in the present invention is an orthogonal (non-cross reacting), site-selective recombinase (OSSR). An OSSR is a recombinase that recognizes a specific recognition site or nucleotide sequence and does not cross-react with the recognition site or nucleotide sequence of another recombinase. In some embodiments, each recombinase recognizes a pair of identical DNA sequences is that is about 50 to 60 basepair in length. In some embodiments, the recombinase recognizes a pair of identical DNA sequences is that is about 52 to 58 basepair in length. In some embodiments, the recombinase recognizes a pair of identical DNA sequences is that is about 53, 54, 55, 56 or 57 basepair in length. If only two sites are present, and they are oriented in the same direction on a DNA strand, the sequence between the sites is excised into a loop, with one recognition site remaining on the annealed DNA and one site incorporated into the loop. If more than two sites are present, or the orientation between sites is different, multiple activities can occur, including flipping and mis-annealing of the genomic DNA.

Figure 10:
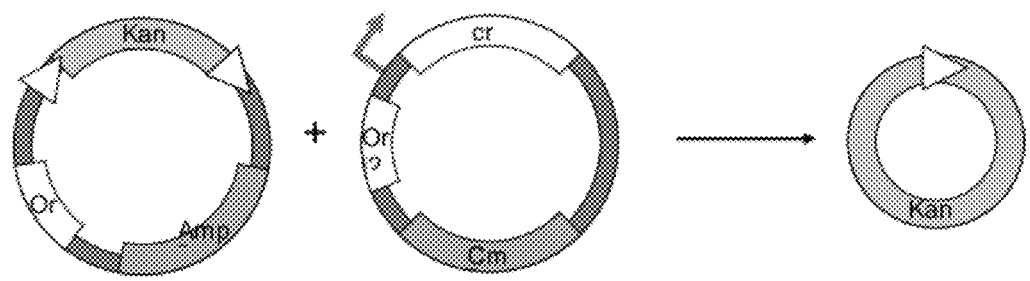
FIG. 10 shows a screen based on excision events. In this example, reactive pairs are identified by replica plating from ampicillin (Amp)/chloramphenicol (Cm) plates to kanamycin (Kan)/Cm plates.
Figure 11:
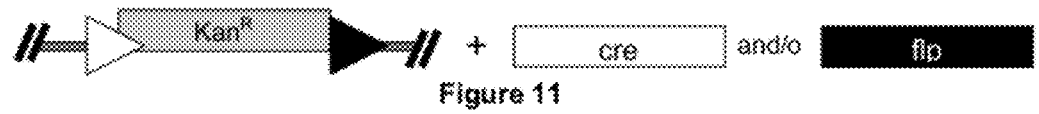
FIG. 11 shows a representative testing of cross pairs and simultaneous expression. A large number of constructs is required (ΣN for N recognition sites +2 per recombinase using a three plasmid system) and extensive cross testing.

To be useful for the present invention, the recombinase and its recognition sites must display the following properties: (1) Engineered recognition sites should be unique to the cell (that is, no native genomic sequence matches the recognition site). (2) Recombinases must not bind to the recognition sites associated with other recombinases. (3) Recombinases bound to a recognition site must not be able to bind to the "partner" recombinase associated with a different recognition site. (The functional unit of a recombinase is a dimer of dimers. For example, dimer AA normally binds to site a. This then interacts with another dimer AA bound to a different site a to cause a recombination event. If dimer AA recognizes site a, and dimer BB recognizes site b, if AA is capable of binding to BB in the presence of a and b, a cross reaction would occur.) (4) Recognition sites should be kept to a total of two per cell per recombinase in all cases where this is possible during the operation of the invention. FIG. 9 shows an example of cross pairing (of three different recombinases) which should not result in excision. FIG. 10 shows a screen based on excision events. FIG. 11 shows a representative testing of cross pairs and simultaneous expression.

Recombinases useful for this invention include, but are not limited to, to the recombinases listed in Table 1.

TABLE 1

Recombinases.

| # | Name | Host | Organism | Gene | Accession |
|---|------|------|----------|------|-----------|
| 1 | BSu_xerC | *Bacillus subtilis* | chromosome | codV | P39776 |
| 2 | BSu_xerD | *Bacillus subtilis* | chromosome | ripX | P46352 |
| 3 | BSu_ydcL | *Bacillus subtilis* | chromosome | ydcL | A69774 |
| 4 | CBu_tnpA | *Clostridium butyricum* | chromosome | tnpA | S40097 |
| 5 | ColID | *Escherichia coli* | plasmid F | D | P06615 |
| 6 | CP4-57 | *Escherichia coli* | chromosome | Int | P32053 |
| 7 | Cre | *Escherichia coli* | phage P1 | Int | P06956 |
| 8 | D29 | *Mycobacterium smegmatis* | phage D29 | Int | AAC18476 |
| 9 | DLP12 | *Escherichia coli* | phage DLP12 | Int | P24218 |
| 10 | DNo_int | *Dichelobacter nodosus* | chromosome | Orf | AAB00935 |
| 11 | ECo_fimB | *Escherichia coli* | chromosome | fimB | P04742 |
| 12 | ECo_fimE | *Escherichia coli* | chromosome | fimE | P04741 |
| 13 | ECo_orf | *Escherichia coli* | chromosome | b2442 | A65019 |
| 14 | ECo_xerC | *Escherichia coli* | chromosome | xerC | C37841 |
| 15 | ECo_xerD | *Escherichia coli* | chromosome | xerD | P21891 |
| 16 | HIn_orf | *Haemophilus influenzae* | chromosome | orf1572 | P46495 |
| 17 | HIn_rci | *Haemophilus influenzae* | chromosome | rci | P45198 |
| 18 | HIn_xerC | *Haemophilus influenzae* | chromosome | xerC | P44818 |
| 19 | HIn_xerD | *Haemophilus influenzae* | chromosome | xerD | P44630 |
| 20 | HK22 | *Escherichia coli* | phage HK022 | int | AAF30377 |
| 21 | HP1 | *Haemophilus influenzae* | phage HP1 | int | P21442 |

TABLE 1-continued

Recombinases.

| # | Name | Host | Organism | Gene | Accession |
|---|---|---|---|---|---|
| 22 | L2 | *Acholeplasma* sp. | phage L2 | int | AAA87961 |
| 23 | L5 | *Mycobacterium tuberculosis* | phage L5 | int | CAA79409 |
| 24 | L54 | *Staphylococcus aureus* | phage L54 | int | P20709 |
| 25 | Lambda | *Escherichia coli* | phage lambda | int | AAA96562 |
| 26 | LLe_orf | *Lactobacillus leichmannii* | chromosome | orf | CAA55635 |
| 27 | LLe_xerC | *Lactobacillus leichmannii* | chromosome | xerC | CAA59018 |
| 28 | phi10MC | *Oenococcus oeni* | phage phi10MC | int | AAD00268 |
| 29 | MJa_orf | *Methanococcus jannaschi* | chromosome | orf | Q57813 |
| 30 | MLe_xerD | *Mycobacterium leprae* | chromosome | xerD | S72959 |
| 31 | MPa_int | *Mycobacterium paratuberculosis* | chromosome | int | AAA88834 |
| 32 | MTu_int | *Mycobacterium tuberculosis* | chromosome | int | B70965 |
| 33 | MTu_xerC | *Mycobacterium tuberculosis* | chromosome | xerC | Q10815 |
| 34 | MV4 | *Lactobacillus delbrueckii* | phage MV4 | int | AAC48859 |
| 35 | MX8 | *Myxococcus xanthus* | phage Mx8 | int | AAC48895 |
| 36 | pAE1 | *Alcaligenes eutrophus* | plasmid pAE1 | orf | AAA87238 |
| 37 | pCL1 | *Chlorobium limicola* | plasmid pCL1 | fim | AAB36935 |
| 38 | pDU1 | *Nostoc* sp. | plasmid pDU1 | orf | AAA17517 |
| 39 | pMEA | *Amycolatopsis methanolica* | plasmid pMEA300 | orf | AAB00469 |
| 40 | RSp_EF | *Rhizobium* sp. | plasmid pNG234a | EF | P55429 |
| 41 | RSp_GC | *Rhizobium* sp. | plasmid pNG234a | GC | P55459 |
| 42 | RSp_QK | *Rhizobium* sp. | plasmid pNG234a | QK | P55632 |
| 43 | RSp_RA | *Rhizobium* sp. | plasmid pNG234a | RA | AAB92467 |
| 44 | RSp_RB | *Rhizobium* sp. | plasmid pNG234a | RB | P55635 |
| 45 | RSp_RC | *Rhizobium* sp. | plasmid pNG234a | RC | P55636 |
| 46 | RSp_RD | *Rhizobium* sp. | plasmid pNG234a | RD | P55637 |
| 47 | RSp_RE | *Rhizobium* sp. | plasmid pNG234a | RE | P55638 |
| 48 | RSp_RF | *Rhizobium* sp. | plasmid pNG234a | RF | P55639 |
| 49 | pSAM2 | *Streptomyces ambofaciens* | plasmid pSAM2 | orf | P15435 |
| 50 | pSDL2 | *Salmonella dublin* | plasmid pSDL2 | resV | A38114 |
| 51 | pSE101 | *Saccharopolyspora erythraea* | plasmid pSE101 | orf | S41725 |
| 52 | pSE211 | *Saccharopolyspora erythraea* | plasmid pSE211 | orf | P22877 |
| 53 | pWS58 | *Lactobacillus delbrueckii* | plasmid pWS58 | orf | CAA90472 |
| 54 | phi-11 | *Staphylococcus aureus* | phage phi11 | int | AAA32198 |
| 55 | phi-13 | *Staphylococcus aureus* | phage phi13 | int | S52761 |
| 56 | phi-80 | *Escherichia coli* phage | phage phi80 | int | CAA27683 |
| 57 | phi-adh | *Lactobacillus gasseri* | phage phiadh | int | JN0535 |
| 58 | phi-CTX | *Pseudomonas aeruginosa* | phage phiCTX | int | CAA74224 |
| 59 | phi-g1e | *Lactobacillus* sp. | phage phi-g1e | int | T13182 |
| 60 | phi-LC3 | *Lactococcus lactis* | phage phiLC3 | int | A47085 |
| 61 | phi-R73 | *Escherichia coli* | phage phi-R73 | int | A42465 |
| 62 | P186 | *Escherichia coli* | phage 186 | int | AAC34175 |
| 63 | P2 | *Escherichia coli* | phage P2 | int | AAD03297 |
| 64 | P21 | *Escherichia coli* | phage P21 | int | AAC48886 |
| 65 | P22 | *Salmonella typhimurium* | phage P22 | int | AAF75002 |
| 66 | P4 | *Escherichia coli* | phage P4 | int | CAA29379 |
| 67 | P434 | *Escherichia coli* | phage 434 | int | P27078 |
| 68 | PAe_xerC | *Pseudomonas aeruginosa* | chromosome | sss | AAG08665 |
| 69 | PMi_fimB | *Proteus mirabilis* | chromosome | fimB | CAB61438 |
| 70 | R721 | *Escherichia coli* | plasmid IncI2 (R721) | rcb | G45252 |
| 71 | Rci | *Escherichia coli* | plasmid IncI1 (R64) | rci | P10487 |
| 72 | SF6 | *Shigella flexneri* | phage Sf6 | int | P37317 |
| 73 | SLP1 | *Streptomyces coelicolor* | plasmid SLP1 | orf | CAC08268 |
| 74 | IntI3 | *Serratia marcescens* | chromosome | orf | BAA08929 |
| 75 | SsrA | *Methanosarcina acetivorans* | plasmid pC2A | ssrA | AAB39744 |
| 76 | SSV1 | *Sulfolobus* sp. | phage SSV1 | int | CAA30211 |
| 77 | T12 | *Streptococcus pyogenes* | phage T12 | int | AAC488867 |
| 78 | IntI1 | *Escherichia coli* | transposon Tn21 | int | AAA82254 |
| 79 | Tn4430 | *Bacillus thuringiensis* | transposon Tn4430 | int | CAA30491 |
| 80 | Tn5041 | *Pseudomonas* sp. | transposon Tn5041 | orfI | CAA67462 |
| 81 | Tn5252 | *Streptococcus pneumoniae* | transposon Tn5252 | int | A55863 |

TABLE 1-continued

Recombinases.

| # | Name | Host | Organism | Gene | Accession |
|---|------|------|----------|------|-----------|
| 82 | Tn5276 | *Lactobacillus lactis* | Tn5276 transposon | int | C55205 |
| 83 | Tn554a | *Staphylococcus aureus* | Tn554 transposon | tnpA | P06696 |
| 84 | Tn554b | *Staphylococcus aureus* | Tn554 | tnpB | P06697 |
| 85 | IntI2 | *Escherichia coli* | transposon Tn7 transposon | int | CAA05031 |
| 86 | Tn916 | *Entercoccus faecalis* | Tn916 | int | P22886 |
| 87 | Tuc | *Lactobacillus lactis* | phage Tuc2009 | int | AAA32608 |
| 88 | BZo_int | *Bergeyella zoohelcum* | chromosome | orf | AAA50502 |
| 89 | ASp_xisA | *Anabaena* sp. | chromosome | xisA | P08862 |
| 90 | ASp_xisC | *Anabaena* sp. | chromosome | xisC | Q44217 |
| 91 | FLP | *Saccharomyces cerevisiae* | plasmid 2μ | FLP | J01347 |
| 92 | pKD1 | *Kluyveromyces lactis* | plasmid pKD1 | FLP | P13783 |
| 93 | pSB2 | *Zygosaccharomyces bailii* | plasmid pSB2 | FLP | M18274 |
| 94 | pSB3 | *Zygosaccharomyces bisporus* | plasmid pSB3 | FLP | P13784 |
| 95 | pSM1 | *Zygosaccharomyces fermentati* | plasmid pSM1 | FLP | P13770 |
| 96 | pSR1 | *Zygosaccharomyces rouxii* | plasmid pSR1 | FLP | P13785 |
| 97 | HPy_xerC | *Helicobacter pylori* | chromosome | xerC | C64604 |
| 98 | HPy_xerD | *Helicobacter pylori* | chromosome | xerD | C64644 |
| 99 | Eco_Rac | *Escherichia coli* | chromosome | int | P76056 |
| 100 | Eco_Qin | *Escherichia coli* | chromosome | int | P76168 |
| 101 | CP4-6 | *Escherichia coli* | chromosome | orf | P71928 |
| 102 | E14 | *Escherichia coli* | chromosome | int | P75969 |
| 103 | MGo_orf | *Mycobacterium gordonae* | chromosome | orf | AAB54012 |
| 104 | MLe_xerC | *Mycobacterium leprae* | chromosome | xerC | CAB10656 |
| 105 | MTu_xerD | *Mycobacterium tuberculosis* | chromosome | xerD | CAB10958 |
| 106 | pEAF | *Escherichia coli* | plasmid EAF | rsv | AAC44039 |
| 107 | PF1_xerC | *Pseudomonas fluorescens* | chromosome | sss | T10461 |
| 108 | PWi_orf | *Protothera wickerhamii* | mitochondria | ymf42 | T11912 |
| 109 | Sfi21 | *Streptococcus thermophilus* | phage Sfi21 | int | AAD44095 |
| 110 | phi-rlt | *Lactobacillus lactis* | phage rlt | int | AAB18676 |
| 111 | STy_xerC | *Salmonella typhimurium* | chromosome | xerC | P55888 |
| 112 | STy_xerD | *Salmonella typhimurium* | chromosome | xerD | P55889 |
| 113 | SSp_orf | *Synechocystis* sp. | chromosome | orf | BAA16682 |
| 114 | DNo_orf | *Dichelobacter nodosus* | chromosome | orf | AAB00935 |
| 115 | VCh_orf | *Vibrio cholerae* | chromosome | orf | AAC44230 |
| 116 | MMa_xerC | *Methanothermobacter marburgensis* | chromosome | xerC | D69219 |
| 117 | ECo_orf2 | *Escherichia coli* | chromosome | intB | P39347 |
| 118 | SIn_orf | *Salmonella infantis* | chromosome | orf | J03391 |
| 119 | BK-T | *Lactococcus lactis* | phage BK-T | int | T13262 |
| 120 | phi-42 | *Staphylococcus aureus* | phage phi42 | int | AAA91615 |
| 121 | FRAT1 | *Mycobacterium* sp. | phage FRAT1 | int | P25426 |
| 122 | HZe_vlf1 | *Helicoverpa zea* | chromosome | vlf1 | AAA58702 |
| 123 | pKW1 | *Kluveromyces waltii* | plasmid pKW1 | FLP | X56553 |
| 124 | CBu_tnpB | *Clostridium butyricum* | chromosome | tnpB | S40098 |
| 125 | S2 | *Haemophilus influenzae* | phage S2 | int | CAA96221 |
| 126 | NBU1 | *Bacteroides uniformis* | plasmid NBU1 transposon | int | AAF74437 |
| 127 | Tn1545 | *Streptococcus pneumoniae* | Tn1545 | int | P27451 |
| 128 | T270 | *Streptococcus pyogenes* | phage T270 | int | AAA85500 |
| 129 | PMi_xerC | *Proteus mirabilis* | chromosome | xerC | AAB87500 |
| 130 | PMi_xerD | *Proteus mirabilis* | chromosome | xerD | AAB87499 |
| 131 | phiV | *Shigella flexneri* | phage V | int | AAB72135 |
| 132 | O1205 | *Streptococcus thermophilus* | phage O1205 transposon | int | T13289 |
| 133 | Tn4556 | *Streptomyces fradiae* | Tn4556 | int | P20184 |
| 134 | MS6 | *Mycobacterium* sp. | phage Ms6 plasmid | int | AAD03774 |
| 135 | pFAJ | *Rhodococcus erythropolis* | pFAJ2600 | pmrA | AAC45806 |
| 136 | SMa_xerC | *Serratia marcescens* | chromosome plasmid | xerC | AAC46276 |
| 137 | pTiA6 | *Agrobacterium tumefaciens* | pTiA6NC | int | AAB91569 |
| 138 | AAe_orf | *Aquifex aeolicus* | chromosome transposon | int | G70397 |
| 139 | Tn557 | *Staphylococcus aureus* | Tn557 | int | AAC28969 |
| 140 | EAe_int | *Enterobacter aerogenes* | chromosome | int | AAB95339 |
| 141 | SF2 | *Shigella flexneri* | phage Sf2 | int | AAC39270 |
| 142 | ECo_yfdB | *Escherichia coli* | chromosome | yfdB | P37326 |
| 143 | RP3 | *Streptomyces rimosus* | phage RP3 | int | X80661 |
| 144 | VWB | *Streptomyces venezuelae* | phage VWB | int | CAA03882 |
| 145 | SEx_vlf1 | *Spodoptera exigua* | chromosome | vlf1 | AAF33611 |
| 146 | STy_rci | *Salmonella typhimurium* | chromosome | rci | AAC38070 |
| 147 | PPu_orf | *Pseudomonas putida* | chromosome | orf | CAA06238 |
| 148 | A2 | *Lactobacillus casei* | phage A2 | int | CAA73344 |

TABLE 1-continued

Recombinases.

| # | Name | Host | Organism | Gene | Accession |
|---|------|------|----------|------|-----------|
| 149 | pECE1 | Aquifex aeolicus | plasmid ece1 | int | AAC07955 |
| 150 | MLo_int | Mesorhizobium loti | chromosome | intS | AAC24508 |
| 151 | SRu_orf | Selenomonas ruminantium | chromosome | orf | BAA24921 |
| 152 | pQPRS | Coxiella burnetti | plasmid pQPRS | int | CAA75853 |
| 153 | PRe_orf | Panagrellus redivivus | chromosome | orf | CAA43185 |
| 154 | CEl_orf | Caenorhabditis elegans | chromosome | orf | Z82079 |
| 155 | IntI4 | Vibrio cholerae | chromosome | intI4 | AAF71178 |
| 156 | SMu_orf | Streptococcus mutans NG8 | chromosome | orfA | AAC17173 |
| 157 | phiU | Rhizobium leguminosarum | phage phiU | int | BAA25885 |
| 158 | PHo_xerC | Pyrococcus horikoshii | chromosome | xerC | B71194 |
| 159 | RCa_orf1 | Rhodobacter capsulatus | chromosome | orf1 | T03499 |
| 160 | RCa_orf2 | Rhodobacter capsulatus | chromosome | orf2 | T03567 |
| 161 | Tn5382 | Enterococcus faecium | transposon Tn5382 | int | AAC34799 |
| 162 | psiM2 | Methanothermobacter marburgensis | phage PsiM2 | int | T12745 |
| 163 | STy_orf | Salmonella typhimurium | chromosome | orf | T03001 |
| 164 | MTu_orf | Mycobacterium tuberculosis | chromosome | Rv2659c | G70966 |
| 165 | TPa_xerC | Treponema pallidum | chromosome | codV | AAC65375 |
| 166 | TPa_xerD | Treponema pallidum | chromosome | xprB | AAC65379 |
| 167 | CTr_xerC | Chlamydia trachomatis | chromosome | xerC | AAC67942 |
| 168 | CTr_xerD | Chlamydia trachomatis | chromosome | xerD | AAC68462 |
| 169 | phiPVL | Staphylococcus aureus | phage phiPVL | int | BAA31902 |
| 170 | pNL1 | Sphingomonas aromaticivorans | plasmid pNL1 | int | AAD03886 |
| 171 | CP4-157 | Escherichia coli O157:H7 | chromosome | int | AAC31482 |
| 172 | SAu_xerD | Staphylococcus aureus | chromosome | xerD | AAC64162 |
| 173 | YPe_orf | Yersinia pestis | chromosome | orf | AAC69581 |
| 174 | RPr_xerD | Rickettsia prowazekii | chromosome | xerD | B71693 |
| 175 | RPr_xerC | Rickettsia prowazekii | chromosome | xerC | B71643 |
| 176 | VCh_SXT | Vibrio cholerae | chromosome | orf | AAF93686 |
| 177 | AAc_orf | Actinob. actinomycetemcomitans | chromosome | orf | AAC70901 |
| 178 | MAV1 | Mycoplasma arthritidis | chromosome | int | AAC33780 |
| 179 | fOg44 | Oenococcus oeni | phage fOg44 | int | AAD10711 |
| 180 | SFX | Shigella flexneri | phage SFX transposon | int | AAD10295 |
| 181 | Tn4371 | Ralstonia eutropha | Tn4371 | int | CAA71790 |
| 182 | HPy_orf | Helicobacter pylori | chromosome | orf | A71869 |
| 183 | CPn_xerC | Chlamydia pneumoniae | chromosome | xerD | BAA99231 |
| 184 | CPn_xerD | Chlamydia pneumoniae | chromosome | xerC | BAA98236 |
| 185 | K139 | Vibrio cholerae | phage K139 | int | AAD22068 |
| 186 | PPu_orf2 | Pseudomonas putida | chromosome plasmid | orf | BAA75916 |
| 187 | pPZG | Pantoea citrea | pPZG500 | int | AAD21210 |
| 188 | H19J | Escherichia coli | phage H19J | int | CAB38715 |
| 189 | phi304L | Corynebacterium glutamicum | phage phi304L | int | CAB38562 |
| 190 | SCo_orf | Streptomyces coelicolor | chromosome | orf | T36198 |
| 191 | phi16 | Corynebacterium glutamicum | phage phi16 | int | CAA73074 |
| 192 | BHa_xerC | Bacillus halodurans | chromosome | codV | BAB06184 |
| 193 | XFa_xerC | Xylella fastidiosa | chromosome | xerC | AAF84292 |
| 194 | BHa_xerD | Bacillus halodurans | chromosome | xerD | BAB05248 |
| 195 | PAe_xerD | Pseudomonas aeruginosa | chromosome | xerD | AAG07125 |
| 196 | VCh_xerC | Vibrio cholerae | chromosome | xerC | AAF93305 |
| 197 | VCh_xerD | Vibrio cholerae | chromosome | xerD | AAF95562 |
| 198 | NMa_xerC | Neisseria meningitidis ser. A | chromosome | xerC | CAB83879 |
| 199 | NMb_xerC | Neisseria meningitidis ser. B | chromosome | xerC | AAF42202 |
| 200 | XFa_xerD | Xylella fastidiosa | chromosome | xerD | AAF84234 |
| 201 | CMu_xerC | Chlamydia muridarum | chromosome | xerC | AAF73578 |
| 202 | SAu_xerC | Staphylococcus aureus | chromosome | xerC | AAF89877 |
| 203 | NMa_xerD | Neisseria meningitidis ser. B | chromosome | xerD | AAF41164 |
| 204 | NMb_xerD | Neisseria meningitidis ser. A | chromosome | xerD | CAB84234 |
| 205 | CMu_xerD | Chlamydia muridarum | chromosome | xerD | AAF39124 |
| 206 | PAb_xerD | Pyrococcus abysii | chromosome | xerD | A75153 |
| 207 | pI3 | Deinococcus radiodurans | plasmid pI3 plasmid | ResU | AAF44051 |
| 208 | pTiSAK | Agrobacterium tumefaciens | TiSAKURA | orf36 | BAA87661 |
| 209 | HPj_xerC | Helicobacter pylori J | chromosome | xerC | B71910 |
| 210 | TMa_xerC | Thermotoga maritima | chromosome | xerC | D72312 |
| 211 | CJe_xerD | Campylobacter jejuni | chromosome | xerD | CAB73128 |
| 212 | APe_xerD | Aeropyrum pernix | chromosome | xerD | G72672 |
| 213 | PSy_orf | Pseudomonas syringae | chromosome | orfF | CAB96970 |
| 214 | MM1 | Streptococcus pneumoniae | phage MM1 | int | CAB96616 |
| 215 | XNi_vlf1 | Xestia nigrum | chromosome | vlf1 | AAF05239 |
| 216 | PXy_vlf1 | Plutella xylostella | chromosome | vlf1 | AAG27387 |
| 217 | pXO1-132 | Bacillus anthracis | plasmid pXO1 transposon | 132 | D59107 |
| 218 | Tn4555 | Bacteroides fragilis | Tn4555 | int | AAB53787 |

TABLE 1-continued

Recombinases.

| # | Name | Host | Organism | Gene | Accession |
|---|------|------|----------|------|-----------|
| 219 | DRa_xer | Deinococcus radiodurans | chromosome | xerD | G75636 |
| 220 | BJa_int | Bradyrhizobium japonicum | chromosome | intA | AAF64651 |
| 221 | BHa_orf4 | Bacillus halodurans | chromosome | BH2349 | BAB06068 |
| 222 | pXO1-103 | Bacillus anthracis | plasmid pXO1 | 103 | G59103 |
| 223 | PAe_orf2 | Pseudomonas aeruginosa | chromosome plasmid | orf2 | AAG04117 |
| 224 | pLGV440 | Chlamydia trachomatis | pLGV440 transposon | orf8 | P08788 |
| 225 | Tn5520 | Bacteroides fragilis | Tn5520 | bipH | AAC80279 |
| 226 | pNL1_tnpA | Sphingomonas aromaticivorans | plasmid pNL1 | tnpA | AAD03922 |
| 227 | CTr_orf | Chlamydia trachomatis | chromosome | orf1 | S44160 |
| 228 | BHa_orf1 | Bacillus halodurans | chromosome | BH3551 | BAB07270 |
| 229 | phi-933W | Escherichia coli | phage 933W | int | AAD25406 |
| 230 | CPs_orf1 | Chlamydia psittaci | chromosome | orf | B39999 |
| 231 | VCh_orf2 | Vibrio cholerae | chromosome | VC1758 | AAF94908 |
| 232 | DRa_orf2 | Deinococcus radiodurans | chromosome | orf2 | F75611 |
| 233 | pCPnE1 | Chlamydophila pneumoniae | plasmid pCPnE1 | orf2 | CAA57585 |
| 234 | ECo_intB | Escherichia coli | chromosome | intB | AAD37509 |
| 235 | UUr_xerC | Ureaplasma urealyticum | chromosome | xerC | AAF30630 |
| 236 | HK97 | Escherichia coli | phage HK97 | int | AAF31094 |
| 237 | TPW22 | Lactococcus sp. | phage TPW22 | int | AAF12706 |
| 238 | APSE-1 | Acyrthosiphon pisum | phage APSE-1 plasmid | int | AAF03981 |
| 239 | pURB500 | Methanococcus maripaludis | pURB500 | int | AAC45247 |
| 240 | SFl_int | Shigella flexneri | chromosome | int | AAD44730 |
| 241 | UUr_xerD | Ureaplasma urealyticum | chromosome | ripX | AAF30551 |
| 242 | Wphi | Escherichia coli | phage Wphi | int | CAB54522 |
| 243 | BHa_orf2 | Bacillus halodurans | chromosome | BH2364 | BAB06083 |
| 244 | SEn_int | Salmonella enterica | chromosome | intI5 | AAG03003 |
| 245 | pCP1 | Deinococcus radiodurans | plasmid pCP1 | xerD | AAF12667 |
| 246 | SCo_int | Streptomyces coelicolor | chromosome | int | CAB71253 |
| 247 | PRi1724 | Agrobacterium rhizogenes | plasmid pRi1724 | orf9 | BAB16128 |
| 248 | SCo_traS | Streptomyces coelicolor | chromosome | traS | T35465 |
| 249 | HPy_orf1 | Helicobacter pylori | chromosome | orf | A71870 |
| 250 | XFa_orf1 | Xylella fastidiosa | chromosome | XF2530 | AAF85328 |
| 251 | UUr_codV | Ureaplasma urealyticum | chromosome | codV | AAF30942 |
| 252 | pXO1-18 | Bacillus anthracis | plasmid pXO1 | 18 | B59093 |
| 253 | CPs_orf2 | Chlamydia psittaci | chromosome | orf2 | A39999 |
| 254 | SPBc2 | Bacillus subtilis | phage SPBc2 | yopP | T12850 |
| 255 | D3 | Pseudomonas aeruginosa | phage D3 | int | AAF04808 |
| 256 | XFa_orf2 | Xylella fastidiosa | chromosome | XF1642 | AAF84451 |
| 257 | XFa_orf3 | Xylella fastidiosa | chromosome plasmid | XF0678 | AAF83488 |
| 258 | pLGV440-2 | Chlamydia trachomatis | pLGV440 | N1 | S01180 |
| 259 | pB171 | Escherichia coli | plasmid pB171 | rsvB | BAA84906 |
| 260 | DRa_orf3 | Deinococcus radiodurans | chromosome | orf | C75509 |
| 261 | CPZ-55 | Escherichia coli | phage CPZ-55 transposon | int | P76542 |
| 262 | ICESt1 | Streptococcus thermophilus | ICESt1 | int | CAB70622 |
| 263 | pGP7-D | Chlamydia trachomatis | plasmid pGP7-D | TCA01 | AAF39715 |
| 264 | XFa_orf4 | Xylella fastidiosa | chromosome | XF1718 | AAF84527 |
| 265 | HIn_orf2 | Haemophilus influenzae | chromosome | int | AAF27347 |
| 266 | DNo_orf2 | Dichelobacter nodosus | chromosome transposon | intC | CAB57348 |
| 267 | NBU2 | Bacteroides fragilis | NBU2 plasmid Col1B-P9 | intN2 | AAF74726 |
| 268 | pColIB | Shigella sonnei | | resA | BAA75108 |
| 269 | PSy_orf4 | Pseudomonas syringiae | chromosome transposon | orf | CAC14205 |
| 270 | Tn4652 | Pseudomonas putida | Tn4652 plasmid | orf5 | AAD44277 |
| 271 | pLGV440-3 | Chlamydia trachomatis | pLGV440 | orf7 | P10561 |
| 272 | pF | Escherichia coli | plasmid F | int | BAA97902 |
| 273 | BHa_orf3 | Bacillus halodurans | chromosome | BH4039 | BAB07758 |
| 274 | XFa_orf5 | Xylella fastidiosa | chromosome plasmid | XF2132 | AAF84931 |
| 275 | pNRC100_1 | Halobacterium sp. | pNRC100 | H0618 | T08273 |
| 276 | SDy_orf | Shigella dysenteriae | chromosome | int | AAF28112 |
| 277 | pQpRS_2 | Coxiella burnetti | plasmid pQpRS | orf410 | CAA75839 |
| 278 | PMu_rci | Pasteurella multocida | chromosome | rci | AAF68420 |
| 279 | SPBc2 | Bacillus subtilis | phage SPBc2 | yomM | AAC13009 |
| 280 | PPa_int | Pseudomonas pavonaceae | chromosome plasmid | intP | CAB65361 |
| 281 | pKLC102 | Pseudomonas aeruginosa | pKLC102 | xerC | AAG02084 |
| 282 | XFa_orf6 | Xylella fastidiosa | chromosome | XF0631 | AAF83441 |
| 283 | SCo_orf3 | Streptomyces coelicolor | chromosome | int | CAC14368 |

TABLE 1-continued

Recombinases.

| # | Name | Host | Organism | Gene | Accession |
|---|---|---|---|---|---|
| 284 | LLa_orf | *Lactococcus lactis* | chromosome | orf3 | AAF86683 |
| 285 | MSp_orf | *Mycobacterium* sp. | chromosome | intM | CAB65286 |
| 286 | pNL1_tnpB | *Sphingomonas aromaticivorans* | plasmid pNL1 | tnpB | AAD03921 |
| 287 | XFa_orf7 | *Xylella fastidiosa* | chromosome | XF0968 | AAF83778 |
| 288 | ECo_orf5 | *Escherichia coli* | chromosome | int | AAF06962 |
| 289 | AGe_vlf1 | *Anticarsia gemmatalis* | chromosome | vlf-1 | AAD54607 |
| 290 | pLH1 | *Lactobacillus helveticus* | plasmid pLH1 | orf195 | CAA10964 |
| 291 | SAu_orf2 | *Staphylococcus aureus* | chromosome | orf | AAG29618 |
| 292 | LDi_vlf1 | *Lymantria dispar* | chromosome | vlf-1 | AAC70272 |
| 293 | OPs_vlf1 | *Orgyia pseudotsugata* | chromosome | vlf-1 | AAC59079 |
| 294 | SCo_orf2 | *Streptomyces coelicolor* | chromosome | int | CAC08306 |
| 295 | BBu_orf | *Borrelia burgdorferi* | chromosome | orf6 | AAC34963 |
| 296 | pNOB8 | *Sulfolobus* sp. | plasmid pNOB8 | orf101 | T31031 |
| 297 | pMT1 | *Yersinia pestis* | plasmid pMT1 | T1101 | T15016 |
| 298 | ACa_vlf1 | *Autographica californica* | chromosome | vlf-1 | AAA66707 |
| 299 | VCh_orf3 | *Vibrio cholerae* | chromosome | VC0821 | AAF96190 |
| 300 | BMo_vlf1 | *Bombyx mori* | chromosome | vlf-1 | AAC63749 |
| 301 | phi-PV83 | *Staphylococcus aureus* | phage PV83 | int | BAA97808 |
| 302 | PGi_orf | *Porphyromonas gingivalis* | chromosome | orf6 | BAA35089 |
| 303 | AFu_orf | *Archaeoglobus fulgidus* | chromosome | AF0082 | B69260 |
| 304 | pCHL1 | *Chlamydia trachomatis* | plasmid pCHL1 | orf7 | AAA91567 |
| 305 | pR27 | *Salmonella typhi* | plasmid R27 | orf | AAF70020 |
| 306 | APe_orf | *Aeropyrum pernix* | chromosome | APE0818 | E72674 |
| 307 | PSy_orf2 | *Pseudomonas syringiae* | chromosome | orfA | CAB96965 |
| 308 | pNRC100_2 | *Halobacterium* sp. | plasmid pNRC100 | H0928 | T08297 |
| 309 | MJa_orf2 | *Methanococcus jannaschi* | chromosome | MJ0770 | Q58180 |
| 310 | phi16-3 | *Rhizobium* sp. | phage 16-3 | int | CAB54831 |
| 311 | pCP32-1 | *Borrelia burgdorferi* | plasmid cp32-1 | BBP37 | AAF07426 |
| 312 | SAl_orf | *Streptomyces albus* | chromosome | orf | AAD46512 |
| 313 | pNRC100_3 | *Halobacterium* sp. | plasmid pNRC100 | H1373 | T08333 |
| 314 | VCh_orf4 | *Vibrio cholerae* | chromosome | VC0185 | AAF93361 |
| 315 | Tec2 | *Euplotes crassus* | transposon Tec2 | orf2B | AAA91341 |
| 316 | Tec1 | *Euplotes crassus* | transposon Tec1 | orf2B | AAA91341 |
| 317 | PPu_orf3 | *Pseudomonas putida* | chromosome | orf101 | CAB54061 |
| 318 | pCP32 | *Borrelia hermsii* | plasmid cp32 | orf6 | AAF28881 |
| 319 | NMe_int | *Neisseria meningitidis* | chromosome | int | CAB84481 |
| 320 | pCP32-4 | *Borrelia burgdorferi* | plasmid cp32-4 | BBR38 | AAF07512 |
| 321 | pCP18 | *Borrelia burgdorferi* | plasmid cp18 | orf6 | AAB63432 |
| 322 | pCP18-2 | *Borrelia burgdorferi* | plasmid cp18-2 | orf27 | AAF29799 |
| 323 | Tn5401 | *Bacillus thuringensis* | transposon Tn5401 | int | P27451 |
| 324 | SMi_xerD | *Streptococcus mitis* | chromosome | xerD | CAC19443 |
| 325 | SPn_xerD | *Streptococcus pneumoniae* | chromosome | xerD | CAC19448 |
| 326 | EFa_orf | *Enterococcus faecium* | chromosome | intD | AAG42074 |
| 327 | VT1 | *Escherichia coli* O157:H7 | phage VT1-Sakai | int | BAB19626 |
| 328 | psiM100 | *Methanothermobacter wolfeii* | phage psiM100 | int | AAG39942 |
| 329 | CP-933C | *Escherichia coli* O157:H7 | phage 933C | Z1835 | AAG55933 |
| 330 | CP-933I | *Escherichia coli* O157:H7 | phage 933I | Z0324 | AAG54584 |
| 331 | CP-933M | *Escherichia coli* O157:H7 | phage 933M | Z1323 | AAG55457 |
| 332 | CP-933U | *Escherichia coli* O157:H7 | phage 933U | intU | AAG57039 |
| 333 | CP-933T | *Escherichia coli* O157:H7 | phage 933T | intT | AAG56898 |
| 334 | CP-933N | *Escherichia coli* O157:H7 | phage 933N | intN | AAG55869 |
| 335 | CP-933O | *Escherichia coli* O157:H7 | phage 933O | intO | AAG56112 |
| 336 | bIL310 | *Lactococcus lactis* | phage bIL310 | orf1 | AAK08405 |
| 337 | bIL311 | *Lactococcus lactis* | phage bIL311 | int | AAK08433 |
| 338 | SPy_orf5 | *Streptococcus pyogenes* | chromosome | int4 | AAK34767 |
| 339 | bIL309 | *Lactococcus lactis* | phage bIL309 | int | AAK08349 |
| 340 | bIL312 | *Lactococcus lactis* | phage biL312 | int | AAK08454 |
| 341 | SPy_orf2 | *Streptococcus pyogenes* | chromosome | int3 | AAK33851 |
| 342 | SPy_orf4 | *Streptococcus pyogenes* | chromosome | int2 | AAK34288 |
| 343 | bIL286 | *Lactococcus lactis* | phage bIL286 | int | AAK08288 |
| 344 | LLa_xerD | *Lactococcus lactis* | chromosome | xerD | AAK04743 |
| 345 | LLa_ymfD | *Lactococcus lactis* | chromosome | ymfD | AAK05330 |
| 346 | SPy_orf3 | *Streptococcus pyogenes* | chromosome | spy1196 | AAK34058 |
| 347 | SPy_orf1 | *Streptococcus pyogenes* | chromosome | spy0365 | AAK33410 |
| 348 | LLa_orf2 | *Lactococcus lactis* | chromosome | ynbA | AAK05376 |
| 349 | ECo_orf7 | *Escherichia coli* O157:H7 | chromosome | Z4313 | AAG58098 |
| 350 | ECo_orf6 | *Escherichia coli* O157:H7 | chromosome | Z1120 | AAG55265 |
| 351 | pMLa | *Mesorhizobium loti* | plasmid pMLa | mll9356 | BAB54967 |
| 352 | pMLb | *Mesorhizobium loti* | plasmid pMLb | mlr9649 | BAB54839 |
| 353 | pRi_orf2 | *Rhizobium rhizogenes* | plasmid pRi | ri136 | BAB16255 |
| 354 | MLo_orf1 | *Mezorhizobium loti* | chromosome | mll8495 | BAB54366 |
| 355 | MLo_orf2 | *Mezorhizobium loti* | chromosome | mll7973 | BAB53631 |

TABLE 1-continued

Recombinases.

| # | Name | Host | Organism | Gene | Accession |
|---|---|---|---|---|---|
| 356 | MLo_orf3 | *Mezorhizobium loti* | chromosome | mlr7741 | BAB54140 |
| 357 | MLo_orf4 | *Mezorhizobium loti* | chromosome | mlr6952 | BAB53138 |
| 358 | SEn_orf2 | *Salmonella enterica* | chromosome | int2 | AF261825 |
| 359 | MLo_orf5 | *Mezorhizobium loti* | chromosome | mll5763 | BAB52151 |
| 360 | ECo_orf8 | *Escherichia coli* | chromosome | ILG1 | AAK49816 |
| 361 | MLo_orf6 | *Mezorhizobium loti* | chromosome | mlr0958 | BAB48432 |
| 362 | CCr_orf1 | *Caulobacter crescentus* | chromosome | CC2681 | AAK24647 |
| 363 | MLo_orf7 | *Mezorhizobium loti* | chromosome | mll4043 | BAB50796 |
| 364 | MLo_orf8 | *Mezorhizobium loti* | chromosome | mll0487 | BAB48065 |
| 365 | MLo_orf9 | *Mezorhizobium loti* | chromosome | mlr0475 | BAB48054 |
| 366 | phi-ETA | *Staphylococcus aureus* | phage phi-ETA | orf1 | BAA97587 |
| 367 | CCr_xerD | *Caulobacter crescentus* | chromosome | CC3006 | AAK24968 |
| 368 | CCr_xerC | *Caulobacter crescentus* | chromosome | CC0344 | AAK22331 |
| 369 | pRVS1 | *Vibrio salmonicida* | plasmid pRVS1 | int | CAC35342 |
| 370 | phiSLT | *Staphylococcus aureus* | phage phi-SLT | int | BAB21695 |
| 371 | SSo_xer | *Sulfolobus solfataricus* | chromosome transposon | xerCD | AAK40704 |
| 372 | CW459 | *Clostridium perfringens* | CW459 | int459 | AAK17958 |
| 373 | MPu_xerC | *Mycoplasma pulmonis* | chromosome | MY5310 | CAC13704 |
| 374 | TVo_xerC | *Thermoplasma volcanium* | chromosome | xerC | BAB59407 |
| 375 | TAc_xerC | *Thermoplasma acidophilum* | chromosome | Tal314 | CAC12435 |
| 376 | TVo_orf1 | *Thermoplasma volcanium* | chromosome | orf1 | BAB59869 |
| 377 | SEn_orf2 | *Salmonella enterica* | chromosome | S020 | AAK02039 |
| 378 | PMu_xerC | *Pasteurella multocida* | chromosome | xerC | AAK03785 |
| 379 | PMu_xerD | *Pasteurella multocida* | chromosome | xerD | AAK02177 |
| 380 | MLo_xerD | *Mesorhizobium loti* | chromosome | mlr3575 | NP_104652 |
| 381 | DRa_orf4 | *Deinococcus radiodurans* | chromosome | xerD | AA-F12544 |
| 382 | HSp_orf1 | *Halobacterium* sp. | chromosome | ssrA | AAG19292 |
| 383 | PMu_orf1 | *Pasteurella multocida* | chromosome | slpA | AAK03853 |
| 384 | PGi_xerC | *Porphyromonas gingivalis* | chromosome | PG1732 | |
| 385 | PGi_xerD | *Porphyromonas gingivalis* | chromosome | PG0386 | |
| 386 | RCa_orf3 | *Rhodobacter capsulatus* | chromosome | orf | U57682 |
| 387 | MLo_orf10 | *Mesorhizobium loti* | chromosome | mlr9321 | NP_085850 |
| 388 | MLo_orf11 | *Mesorhizobium loti* | chromosome | mlr9323 | NP_085851 |
| 389 | MLo_orf12 | *Mesorhizobium loti* | chromosome | mlr9324 | NP_085852 |
| 390 | MLo_orf13 | *Mesorhizobium loti* | chromosome | mll9328 | NP_085856 |
| 391 | MLo_orf14 | *Mesorhizobium loti* | chromosome | mll9329 | NP_085857 |
| 392 | MLo_orf15 | *Mesorhizobium loti* | chromosome | mll9330 | NP_085858 |
| 393 | MLo_orf16 | *Mesorhizobium loti* | chromosome | mll9331 | NP_085859 |

In some embodiments, the suitable recombinases are the recombinases listed as numbers 7, 12, 93, 95, 97, and 98 in Table 1.

A method to identify an OSSR is by determining by identifying the catalytic residues. Identifying orthogonality is done by preparing a plasmid containing a gene of interest (such as Kanamycin resistance) that is flanked by putative recombinase recognition sites. Co-transformation of a cell with this plasmid and a plasmid containing the putative recombinase will either result in excision of the gene of interest or no reaction. If a reaction occurs, the cell will then be susceptible to treatment with Kanamycin. This is identifiable by replica plating of viable colonies onto an agar plate containing Kanamycin.

In some embodiments, an integration construct is constructed that can be integrated into a genome using lambda red (a promiscuous recombinase). The integration construct would comprise a promoter blocked by a terminator, with the terminator flanked by recognition sites of one of the six recombinases. By making competent cell stocks of each cell line, each recombinase gene is added as a plasmid and then the activity of the reporter gene is measured. This would determine if each protein was capable of working on multiple sequences.

The paper "DNA recombination with a heterospecific Cre homolog identified from comparison of the pac-c1 regions of P1-related phages" (Sauer and McDermott, Nucleic Acids Research, 2004, Vol. 32, No. 20, 6086-6095; hereby incorporated by reference) performed a similar experiment using a multi-copy plasmid to check cross reactivity between the recombinase Cre and a homolog protein labeled Dre. A marker for Zeomycin resistance was placed between the recognition sites, and then cell lines were transformed with a separate plasmid containing the recombinase under study, either Cre or Dre. By growing these cells in the presence or absence of the antibiotic, a perfect record of viability was reported. When using the non-cross reacting gene, a perfect record of death was reported when using the appropriate gene to remove the resistance marker. This screen addresses point (2) listed above, that a recombinase will not bind to the recognition sites of another. However, this screen does not determine whether a mixed recognition site package (site cre, GENE, site dre, as well as the reverse) is capable of initiating recombination.

The recombinant nucleic acids of the invention can be constructed using methods well known to one skilled in the art. One such method includes the "West Coast BioBricks System" (BioBricks) for which separate constructs have been made for many recognition sites, promoters, resistance markers, and other biological device pieces. These pieces allow sequential assembly of complicated constructs. Exemplary components useful for the BioBricks system are shown in FIGS. 2-9. Coding Sequences (C) are complete open reading frames (type I), or sequences encoding polypeptides but lacking either a stop codon (type II), a start codon (type III), or both (type IV). Ribosome Binding Sites (RBS) are sequences encoding a ribosome binding site, fused 5' to an ORF part. Terminators (TT) are sequence causing transcription termination.

One can use the BioBricks system to make constructs similar to those described in the referenced paper, with many different recognition sites flanking an antibiotic resistance marker. All relevant combinations will be made for each construct. For example, for recombinases A, B, and C that recognize sites a, b, and c, respectively, the following constructs can be made:

a Resistance Marker1 a//Resistance Marker 2
a Resistance Marker1 b//Resistance Marker 2
a Resistance Marker1 c//Resistance Marker 2
b Resistance Marker1 a//Resistance Marker 2
b Resistance Marker1 b//Resistance Marker 2
b Resistance Marker1 c//Resistance Marker 2
c Resistance Marker1 a//Resistance Marker 2
c Resistance Marker 1 b//Resistance Marker 2
c Resistance Marker1 c.//Resistance Marker 2.

As described above, Marker 1 is removable but Marker 2 is not. Stocks of competent cells are made for each construct. These cells are then transformed with plasmids containing one or more recombinases each to cover all potential combinations. Those plasmids should also harbor resistance marker 3. These transformations are then be plated on agar plates containing antibiotics 2 and 3, and incubated to give rise to resultant colonies. Using the replica plating technique, colonies are then transferred to a plate containing antibiotic 1. Colonies are counted to assess viability.

In some embodiments, the recombinant nucleic acid further comprises a promoter that is upstream of the constructs and is capable of transcribing one or more of the constructs in a suitable host cell.

In some embodiments, the recombinant nucleic acid further comprises one or more target nucleotide sequences that are downstream of the constructs, wherein the one or more target sequences are transcribed when all of the constructs are deleted or excised. The target nucleotide sequences can encode an ORF, interference RNA, antisense RNA, or the like.

In some embodiments, the nucleotide sequence of interest comprises one or more ORF, interference RNA, antisense RNA, or the like, or one or more a terminator, or both thereof.

In some embodiments, the ORF encodes a polypeptide. The polypeptide can be a selective marker, an enzyme, a polypeptide that causes the death of the host cell in which the recombinant nucleic acid is located, or the like.

In some embodiments, each construct can further comprise a terminator located between the nucleotide sequence of interest and the second recognition sequence.

In some embodiments, the construct is located or inserted within two ORFs, that when the construct is excised from the recombinant nucleic acid, the two ORFs form a single ORF encoding a polypeptide of a certain biological function. In some embodiments, the certain biological function is one that causes the death of a host cell comprising the recombinant nucleic acid.

In some embodiment of the present invention, the recombinant nucleic acid comprises a synthetic telomere. The synthetic telomere is one application of multiple OSSRs that function as a counting mechanism for host cell, such as a bacteria, such as *E. coli*. The synthetic telomere makes use of cell cycle sensitive, low level expression of recombinases that, over time, cleaves inhibitory sequences from the genome, and concludes in the expression of a target gene. Such a device requires OSSRs that do not prevent miscounting, or worse, genomic scrambling. In some embodiments, the synthetic telomere is capable of a time dependence that based on the number of OSSRs present. The recombinases can be used to remove a section of the recombinant nucleic acid, such as DNA. Using the synthetic telomere, nucleotide sequence is removed as it is processed, preventing it from being read or interfering with the counting mechanism.

In some applications of the synthetic telomere, the synthetic telomere can function as a fuse that "burns down" until it reaches its target (i.e., the promoter becomes adjacent or operably linked to a gene or nucleotide sequence) and causes the expression of the gene or nucleotide sequence. The expression of the gene or nucleotide sequence can in turn directly or indirectly cause the activation or up regulation of the expression of one or more genes, and/or the repression or down regulation of the expression of one or more genes.

A synthetic teleomere functions as follows: (1) A suitable signal from the cell causes the transcription of the first recombinase. The second recombinase cannot be transcribed because of the presence of a terminator element. (2) Once the recombinase is translated and folded, the gene for the recombinase and the associated terminator element are excised by a recombination event. This DNA loop will be broken down by the host cell. (3) The next time the initiating signal fires, the second recombinase is transcribed. The third recombinase cannot be transcribed because of the presence of a terminator element. (4) The process repeats until all recombinase-terminator elements have been removed, and a reporter gene at the end of the sequence is expressed.

The synthetic teleomere acts as a time delay between the activation of transcription and the expression of a target gene. However, if the signal pulses are associated with a distinct phenomenon, such as cell cycles, night and day, or chemical washes, the invention now serves as a counting mechanism (albeit one that always counts down).

The present invention also provides for a recombinant vector comprising the recombinant nucleic acid. The recombinant nucleic acid can be a double-stranded or single-stranded DNA, or RNA. In some embodiments, the recombinant nucleic acid is integrated into a chromosome of a host cell. In some embodiments, the recombinant nucleic acid can further comprise sequences sufficient for having the recombinant nucleic acid stably replicate in a host cell. The recombinant nucleic acid can be replicon capable of stable maintenance in a host cell. In some embodiments, the replicon is a plasmid. The present invention also provides for a vector or expression vector comprising a recombinant nucleic acid of the present invention.

It will, be apparent to one of skill in the art that a variety of recombinant vectors can be utilized in the practice of aspects of the invention. As used herein, "vector" refers to polynucleotide elements that are used to introduce recombinant nucleic acid into cells for either expression or replication. Selection and use of such vehicles is routine in the art. An "expression vector" includes vectors capable of expressing DNAs that are operatively linked with regulatory sequences, such as promoter regions. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those that integrate into the host cell genome.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes that confer antibiotic resistance or sensitivity.

Methods for introducing the recombinant vectors of the present invention into suitable hosts are known to those of skill in the art and typically include the use of $CaCl_2$ or other agents, such as divalent cations, lipofection, DMSO, protoplast transformation, conjugation, and electroporation.

Activating expression from the promoter results in the expression of the first recombinase which in turn proceeds to recognize the two recognition sequence of the first recombinase and excise or delete the first nucleotide sequence of interest. Activating expression of each respective recombinase results in the recognition of the two recognition sequence of the respective recombinase and the excision or deletion of the corresponding nucleotide sequence of interest.

In some embodiments, the method further comprises: introducing a recombinant nucleic acid into a host cell prior to the providing step, wherein the recombinant nucleic acid comprises at least the first construct and the second construct.

The present invention further provides for a compositions and methods attenuating signal (non-coding RNA interference and Dominant-Negative complexation) by coupling to the activation of a recombinase, an enzyme which can toggle a DNA element between two states. A target DNA element can be designed to, the difference between the two states is essentially arbitrary and almost unlimited. It is not necessary that the same gene product be produced in both states. When used in traditional systems, these signal attenuation methods are limited by the fact that the intensity of the desired output is directly tied to the level of attenuation. When recombinases are used in traditional systems, they are typically limited by the noise generated in attempting to control the recombinase gene, which can cause the switch to enter the improper state. It has not been previously demonstrated that these various devices can be operated in concert to both: (1) have greater control over the properties of both devices, and (2) produce unique genetic devices that would not be possible without the marriage of these functions.

Non-coding RNA interference is a method of preventing protein expression from a given mRNA. by the introduction of a second, non-coding RNA (hereafter ncRNA) that renders the target mRNA unreadable by the protein synthesis machinery. A number of design styles have been used to demonstrate this, but the key component is that the non-coding RNA typically binds the coding RNA in a 1:1 ratio. Thus, an effect is produced in direct proportion with the number of readable copies, where readable copies=(mRNA−(non-coding RNA)), modulated by the binding constant. This system is itself subject to noise near the equivalence point, but is otherwise a very tuneable system.

Dominant-Negative complexation involves intentional production of a non-functional version of the active enzyme (usually a point mutation in the active site) that attenuates the active enzyme in two ways: (1) Competition for the binding site, and (2) Interference in the formation of functional multimers. In both cases, the level of attenuation is a function of concentration of the active enzyme relative to inactive enzyme. However, in systems where every subunit of a complex must be functional to produce an active enzyme (as with recombinases), the multimer effect allows even small amounts of inactive protein to nullify an otherwise-active complex. The intensity of this effect is increased as the number of monomers required in the active complex grows (recombinases are functional tetramers.) Of particular importance is that the recombinase reaction is fully reversible if it does not go to completion! Therefore, a "mixed" multimer of functional and non-functional monomers will not produce a side-product, but will instead continue to suppress function of active multimers by competing for the binding site.

Recombinases are unique among DNA manipulating enzymes for several reasons: (1) The output of their function is digital. When properly designed, the two states can be assigned any arbitrary function. The intensity or type of activation event has no mandatory influence on the two states in any way. It is even possible to toggle a switch between a "sensitive" and "insensitive" state, so that the output can be made dependent or independent to any other control mechanism. (2) The mechanism of action allows for large numbers of recombinases to be used without concern for exhausting available sites or causing cross reactions between multiple sites. Thus one well-designed circuit could easily be adapted for a different output, and multiple circuits could be used in the same cell. This is important in the construction of logic circuits or decision trees that require multiple events recognized over time before a final state is reached. (3) In addition to not interfering with each other, recombinases have a very limited set of required interactions to perform their function: they need to bind identical monomers and bind to DNA. By not involving any other cellular machinery in their function, the system is simplified and the risk of side reactions and cell overload is reduced.

Two different modes of use are possible, integrated/excised or "facing left"/"facing right". To simplify, further circuits are described using the "facing left"/"facing right" convention although this system works with both designs. The main difference between the two modes is that integrated/excised is less reversible and thus less likely to be scrambled. However, it functions by removing a DNA element, so genetic information is lost permanently when the switch is activated. Alternatively, the "facing left/facing right" circuit is reusable, but can lead to scrambling of the switch if not properly controlled.

A system, for noise canceling in recombinase circuits, works as follows (FIG. 14):
1. A constitutive promoter is followed by a non-coding, interfering RNA, producing that RNA at a set level.
2. An inducible promoter is followed by a recombinase gene. This mRNA is interfered with by the product of promoter 1.
3. Leaky expression of the inducible promoter does not lead to recombinase expression, and the switch remains "unflipped"
4. Induction of promoter 2 produces recombinase mRNA in sufficient quantity that it cannot entirely be inhibited, and recombinase is produced.
5. The produced recombinase "flips" the switch.

Another system follows a similar plan, but uses a Dominant-Negative enzyme (FIG. 15):
1. A constitutive promoter is followed by an active-site knockout of a recombinase, producing RNA and protein at a set level.
2. An inducible promoter is followed by a functional recombinase.
3. Leaky expression of the inducible promoter does not lead to recombinase function, and the switch remains "unflipped".

4. Induction of promoter 2 produces recombinase in sufficient quantity that (a) functional tetramers form and (b) can compete with non-functional tetramers for DNA binding sites.

5. The functional recombinase tetramers "flip" the switch.

Figure 16:
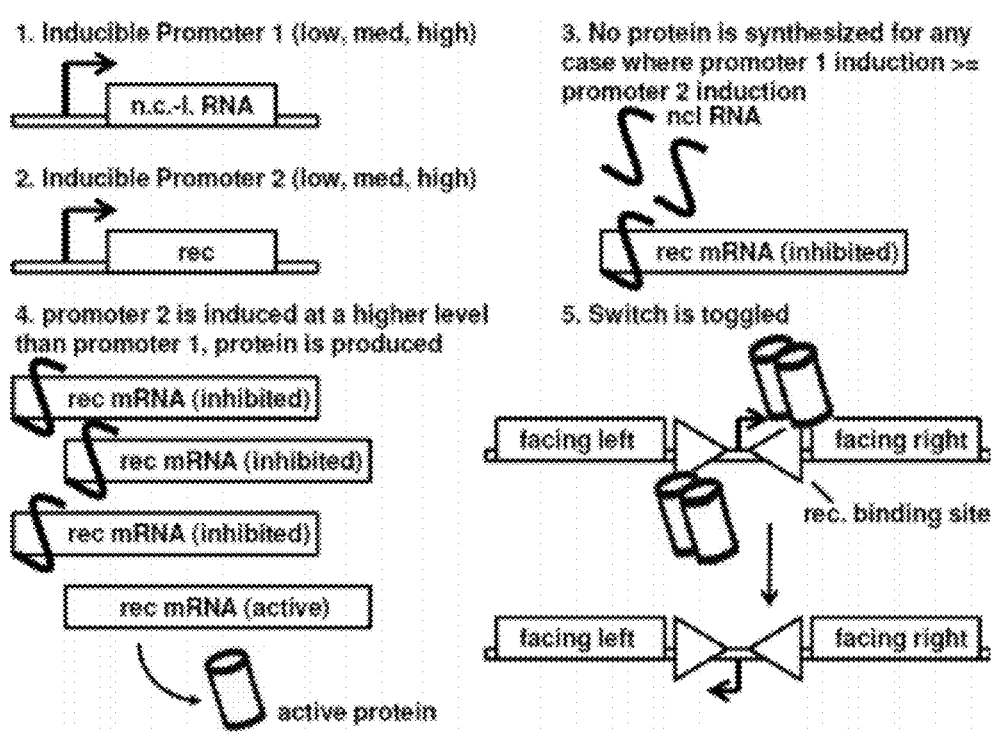
FIG. 16 shows a system comprising a switch that is controlled by the relative expression of two variable promoters
Figure 17:
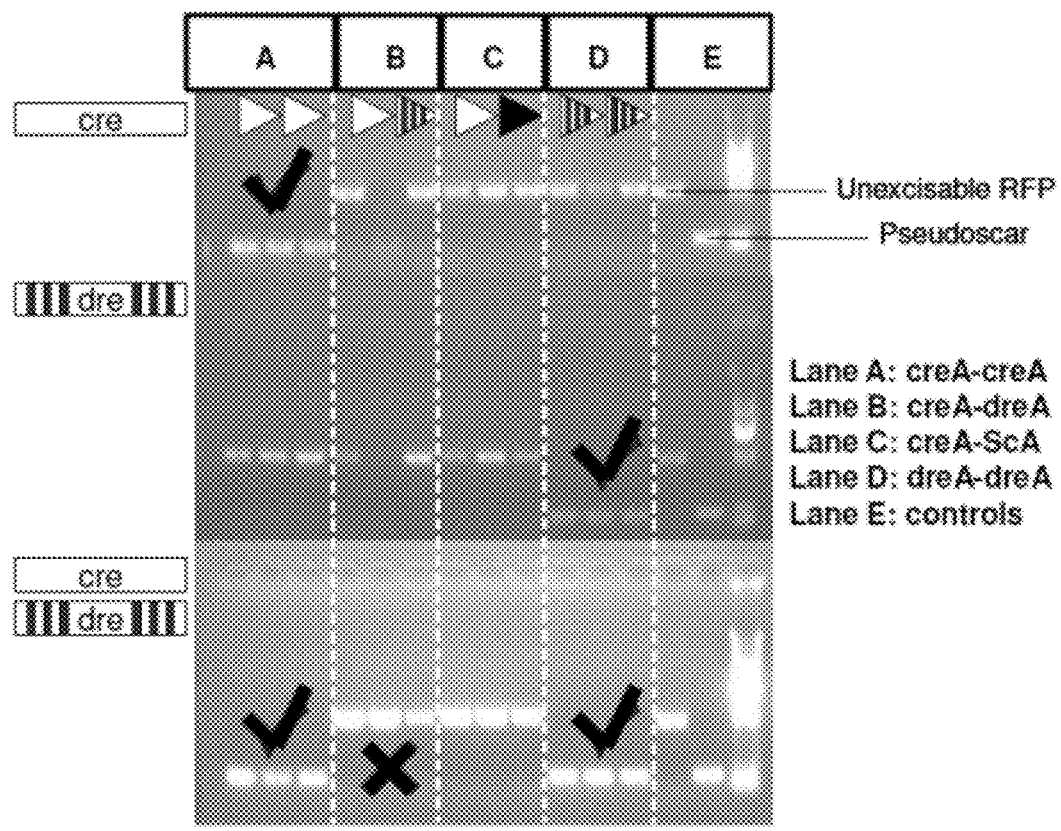
FIG. 17 shows a sample gel showing a cross-test involving Cre, Dre, Cre-Dre and the various site combinations giving the expected results quite cleanly by colony PCR analysis
Figure 18:
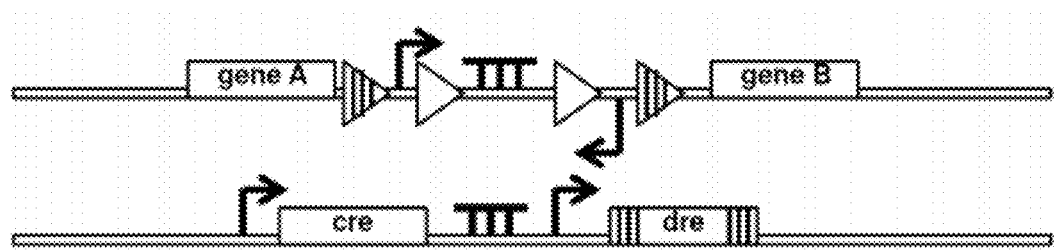
FIG. 18 shows an "or" gate of the present invention.

Note that system requires lower levels of its inhibitory product to cause inhibition. This makes it stronger, but also harder to titrate exact levels. The above two systems allow for noise canceling. By replacing promoter 1 with an inducible promoter, the threshold of activation is no longer a static value, and the amount of induction required for flipping the switch changes based on the cellular environment. This is summarized for both types of systems in FIG. 16. This is an extremely useful and powerful device. The inducible promoters can be of any type, with particular applications that can be tied to the activation and deactivation of different metabolic pathways in the cell because of the sensitivity of measuring relative abundance. The flipping of switches can be tied to growth, or change in carbon or nitrogen source. The systems can be based on either attenuation method.

With careful system construction any two promoters can have an output tied to a change in their expression level ratio rather than in absolute abundance, if they dominant-negative system is used. This is because various ribosome binding sites can be used to alter the relationship between RNA level and protein level to a range where the system responds.

The invention having been described, the following examples are offered to illustrate the subject invention by way of illustration, not by way of limitation.

Example 1

A Fusebox Expression Cassette

Figure 12:
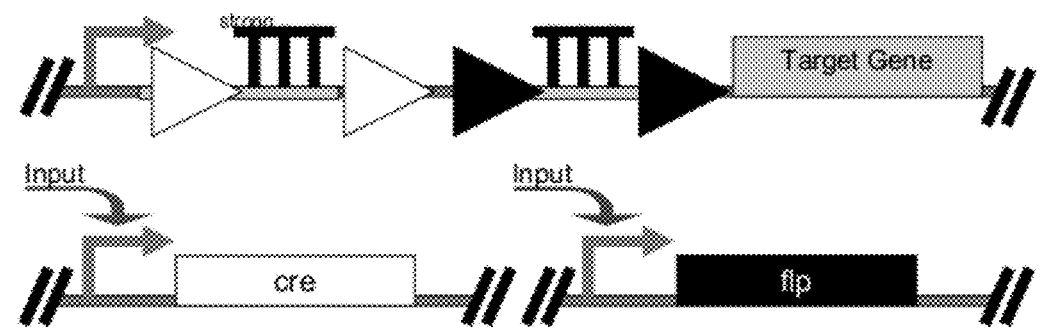
FIG. 12 shows a representative fusebox expression cassette.

An embodiment of the invention is a nucleic acid comprising a nucleotide sequence comprising: promoter—ribosome binding site—recognition site 1a—terminator—recognition site 1b—recognition site 2a—terminator—recognition site 2b—gene of interest, the gene of interest cannot be expressed until the sequence is removed of terminators by treatment with both recombinase 1 and recombinase 2. The expression cassettes for recombinase 1 and 2 do not need to be part of the named construct, nor do they need to be activated simultaneously (hence the name "fusebox"). Once each of the recombinases is activated a single time, it activates a permanent change in cellular state, bringing the cell closer to the expression of the gene of interest. Such a system would allow for multiple, non-simultaneous "checkpoints" to be identified before the gene of interest would be expressed. FIG. 12 shows a representative fusebox expression cassette. A system like this allows for the one-time recognition of multiple signals that result in a permanent change in the cell state. The two (or more) signals do not need to occur simultaneously. This system requires no feedback loop and is low load on the cell.

Example 2

A Synthetic Telomere

Figure 13:
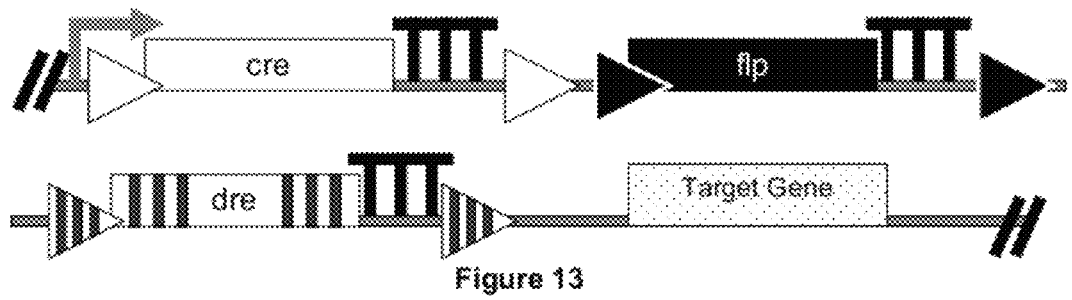
FIG. 13 shows a representative synthetic teleomere.

FIG. 13 shows a representative synthetic teleomere. This device employs recombinases to catalyze the excision of their own gene from a genomic insert. Only one recombinase can be expressed per promoter cycle, resulting in a change in cell state after a given number of events.

Example 3

Cross Testing of Recombinases and Circuit Design

This example demonstrates the efficacy of the cross testing method, initiation the development of our compatibility grid, and the design a circuit using the information thus gained.

Three of the most commonly used (in recombinant systems) recombinases are tested: cre, dre, and FlpSc (here the Sc annotation means from *S. cerevisiae*), each paired with one of their better characterized att sites:

```
lox, acted on by Cre:
                                    (SEQ ID NO: 1)
ATAACTTCGTATAGCATACATTATACGAAGTTAT, rox, acted on by Dre:
                                    (SEQ ID NO: 2)
TAACTTTAAATAATGCCAATTATTTAAAGTTA,
and frt:
                                    (SEQ ID NO: 3)
TTTGAAGTTCCTATTCCGAAGTTCCTATTCTCTAGAAAGTATAGG
AACTT.
```

As multiple sequences for multiple att sites appear across publications, an internal reference code is prepared for each att site. For example, the above sites are referred to as CreA, DreA, and ScA, respectively. This allows keeping track of the various sequences independent of their references while still retaining the reference and sequence information for later publication. It should also be noted that each recombinase has more than a single att site. Most have either two or four, although for commonly used proteins like lox, more are known. These sites need to be cross-tested against each other as well as with att sites that putatively respond to a different recombinase. Such experiments produce independent, non-cross reactive effects across an entire genome with a single enzyme.

Two separate classes of constructs are prepared:
Recombinase constructs: p15A origin, Cm resistance, pTET promoter, and one or two recombinases in an operon.
Att excision constructs: ColE1 origin, Amp resistance, pLacUV5 promoter, attx—Red Fluorescent Protein—atty, where attx and atty are various att recognition sites described above.

These vectors are then co-transformed into *E. coli* strain DH10B, outgrown for one hour in SOC media, and plated on LB plates containing Ampicillin, Chloroamphenicol, IPTG (to induce RFP expression) and aTc (to induce recombinase expression). Although RFP is induced, the constructs are tested using colony PCR to determine if the corresponding part of the test construct is short, indicating an excision product, or long, indicating that RFP has not been excised. These tests can also be performed using more recombinases and att sites, as well as different copy number of the target plasmid and multiple excision targets, including Kan resistance and removal of a terminator that is blocking beta-galactosidase production (i.e. an "on" switch).

Below, these pairs are drawn out in a grid. The grid is filled in with the expected behavior of each crosstest. Table 2 shows the expected cutting patterns for various combinations of recombinases and att sites.

TABLE 2

|  | CreA-CreA | DreA-DreA | ScA-ScA | CreA-ScA | DreA-ScA | CreA-DreA |
|---|---|---|---|---|---|---|
| Cre | cut | no cut | no cut | no cut | no cut | no cut |
| Dre | no cut | cut | no cut | no cut | no cut | no cut |
| FlpSc | no cut | no cut | cut | no cut | no cut | no cut |
| Cre-Dre | cut | cut | no cut | no cut | no cut | no cut |
| Dre-FlpSc | no cut | cut | cut | no cut | no cut | no cut |
| Cre-FlpSc | cut | no cut | cut | no cut | no cut | no cut |

As can be see in the right half of Table 2, the absence of cutting on "mis-matched" att sites is critical to the function of our recombinase circuits. While it would be difficult to test greater numbers of recombinases or sites simultaneously, we hope to map out possible conflicts by analyzing each pairwise combination. If future discrepancies arise in more complicated systems, using this information will allow us to more readily identify the cause of the incompatability.

Figure 14:
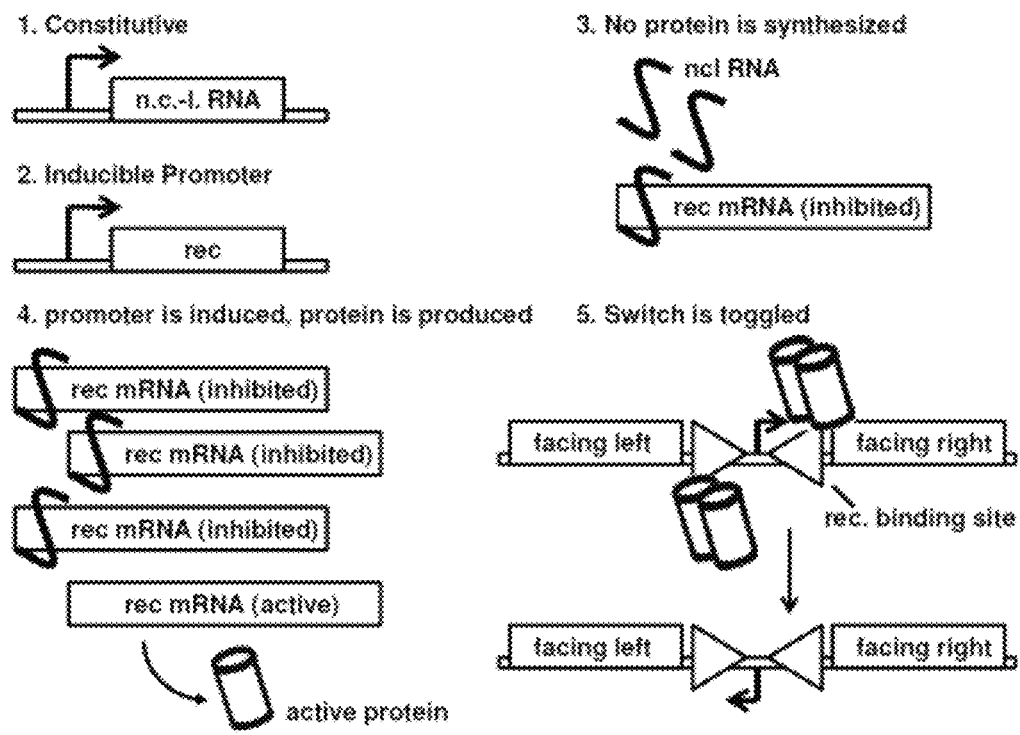
FIG. 14 shows a system capable of noise canceling with non-coding interfering RNA suppression.

FIG. 14 is a sample gel showing the results the above cross tests. The cross-tests involving Cre, Dre, Cre-Dre and the various site combinations give the expected results quite cleanly by colony PCR analysis. FIG. 14 combines three separate gels and is coded to show the excision behavior of the recombinases on the left when expressed in the presence of the att sites shown above, where those att sites are flanking an RFP production cassette. As standards, there are an unexcisable RFP cassette that can be amplified using the same PCR primers as in the experiment, as well as a "pseudoscar" PCR product that corresponds to the size of a CreA-CreA scar after a successful CreA-CreA excision. The PCR primers are universal to the test construct and bind outside of the att sites in order to perform this analysis.

In each set of experiments, the desired behavior is observed. Most importantly, when Cre and Dre are co-expressed, the mixture can correctly excise a CreA-CreA construct, a DreA-DreA construct, but shows no activity on a CreA-DreA construct. This was not necessarily true because the proteins are so similar that antibodies raised to Cre will bind to Dre in a western blot. The exact reason for this relationship is not known, but may have to do with the nature of the Holliday junction resolution (i.e., which nucleotides immediately flank the recombination site) rather than the protein quaternary structure.

A number of cross tests are also performed using FlpSc. Surprisingly, FlpSc is a "bad partner" in crosstests involving Cre. Since FlpSc and Cre are not even in the same subfamily, this behavior is not expected. This result may be related to copy number or att site choice or FlpSc is a less accessible enzyme for advanced circuit design.

The current data of the compatibility grid is in Table 3 below.

TABLE 3

|  | CreA-CreA | DreA-DreA | ScA-ScA | CreA-ScA | DreA-ScA | CreA-DreA |
|---|---|---|---|---|---|---|
| Cre | cut | no cut | some cut | no cut | no cut | no cut |
| Dre | no cut | cut | no cut | no cut | no cut | no cut |
| FlpSc | some cut | no cut | cut | no cut | no cut | no cut |
| Cre-Dre | cut | cut | no cut | no cut | no cut | no cut |
| Dre-FlpSc | no cut | cut | cut | N/D | N/D | N/D |
| Cre-FlpSc | cut | no cut | cut | N/D | N/D | N/D |

It currently appears that both Cre and Dre show some cross activity on at least one att site that is normally associated with the other protein. Although it may be possible to work around this problem by using alternate aft sites, other behaviors of FlpSc suggest that screening other recombinases will prove more immediately fruitful. When FlpSc is co-expressed with another protein, we have been unable to obtain a PCR product when we analyze the colonies. FlpSc may be reacting between sites on multiple plasmids, a behavior reported in the literature for Cre and Dre, but this not yet conclusively verified. The inclusion of copy number variation experiments and changing the reporter to Kanamycin resistance and testing for cell survivability, as described previously, may resolve this.

Figure 15:
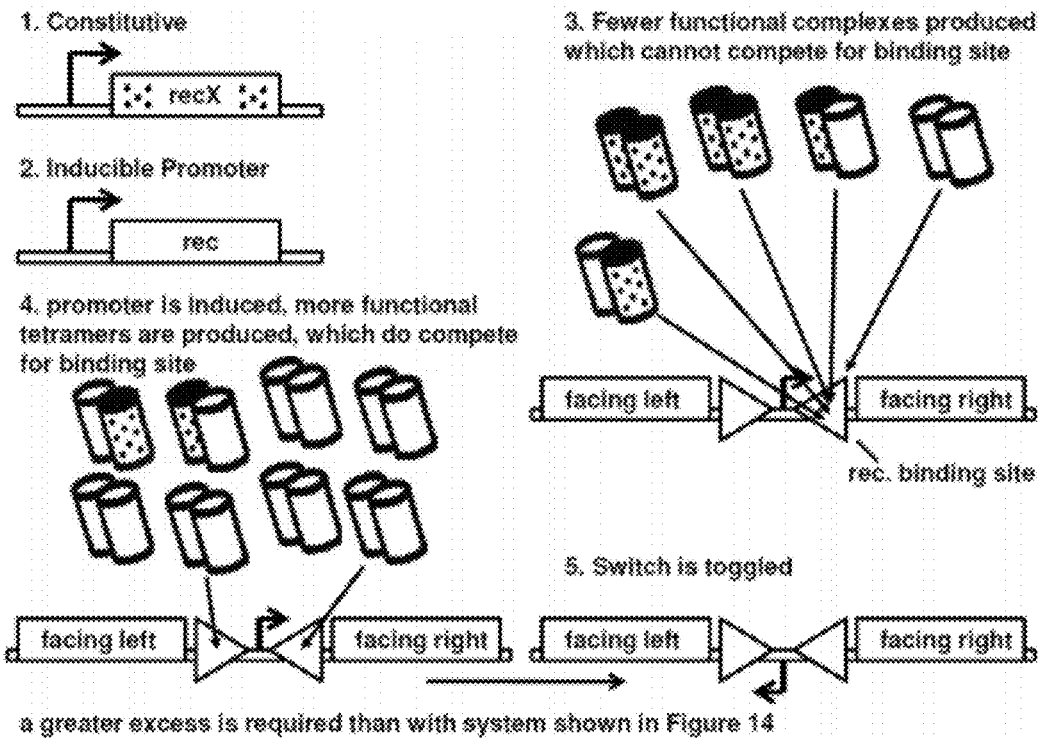
FIG. 15 shows a system capable of noise canceling with dominant negative complexation.
Figure 19:
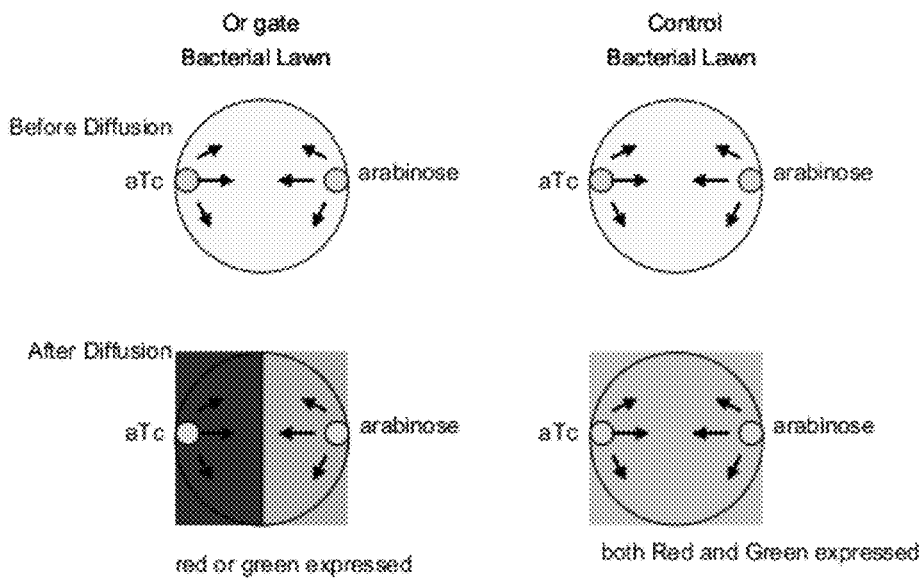
FIG. 19 shows the expected results for a circuit in an agar-plate based assay.

Using the information obtained regarding the compatibilities of Cre and Dre recombinases, an "or" gate is designed as shown in FIG. 15. In this circuit, neither gene A nor gene B can be expressed from their promoters because of the presence of a strong, bi directional terminator in the middle. By differentially expressing either cre or dre, either the white att sites or the striped att sites will excise, respectively. This will allow one of the two target genes to express, but will prevent expression of the other gene by removing its promoter. As described herein, one can control cell fate by differential recombinase expression and can also build towards more complex circuits as additional compatible parings are determined. This circuit for the desired activity can be tested in an agar-plate based assay, where, in the image shown in FIG. 19. The agar-plate based assay comprises the following: Gene A—RFP, Gene B—GFP, promoters in top construct are lacUV5, cre promoter is pTET and dre promoter is pBAD. An agar plate is grown to a lawn, then small disks of filter paper that have been soaked in either aTC (to induce pTET) or arabinose (to induce pBAD) are added to either side of this dish. After diffusion of the inducer, one expects to see a plate as shown below, where no cells produce both fluorescent proteins. As a control, one directly expresses GFP from pBAD and RFP from pTET, in which case the entire plate should express both proteins.

Example 4

New Aft Sites that Make an Orthogonal Pair but Still Respond to an Existing Recombinase As discussed above, the following describes a method for discovering new att sites that make an orthogonal pair but still respond to an existing recombinase. For example, there are many pairs of sites known that the Cre recombinase can act on, but that the individual sites themselves are not competent to resolve, and thus form exclusive pairs. The information gained from performing the crosstesting work, together with sequence information of the known competent pairs of att sites allows one to determine which residues of the crossover region of the att sites generate this site-match specificity that is independent of the recombinase recognition affinity. Increasing the number of att sites that respond to a single recombinase has great potential for introducing genome-wide modifications in a living organism simultaneously and without side-reactions in response to a single stimulus event. Such a tool would be useful both in optimization of fermentative production of small molecules and in the control of genetically engineered organisms in the field, for example plants that begin breaking down their own cellulose in response to a certain signal.

A primary concern in the use of recombinase based circuits is that since the input signal intensity is effectively decoupled from the output signal intensity (i.e. a different promoter can be used for the recombinase and the target gene, as shown in the "or" gate circuit), there may be problems with noise and fidelity. Unlike traditional promoter systems which respond to a variety of inducer concentrations, a recombinase circuit can be a "single fire" system: as soon as the target DNA sequence is excised (or inverted, in some designs), the new circuit becomes active and typically cannot be undone in a controlled fashion. As such controlling more complex circuits requires compensation for this sensitivity and unidirectional. Allowing the att sites and inverted DNA sections to remain in the cell is more likely to scramble the circuit than to allow for the generation of more intricate pathways. However, since the system is effectively completely irreversible, a mechanism is needed to prevent noisy signal from cutting our circuits. This can be done by expressing dominant negative recombinases along side the functional circuits, as described herein, that is using dominant-negative repression and non-coding RNA interference for tuning recombinase based genetic circuits to allow for decoupling of input and output signal strengths by setting a threshold effect (i.e. band-pass filter).

In a simple system, dominant negative recombinase monomers can be expressed with a constitutive promoter of known output. This drastically reduces the chance that 4 functional monomers can access the target sequence and fire until they are in a concentration in excess of the dominant negative monomers. One then measures the ratio of inactive to active monomers that allows activation. Over time, any circuit could fire regardless of the amount of inactive monomer present, so one can test these constructs in longitudinal experiments to assess their stability, which is especially relevant for field applications. The dominant negative recombinases are expected to be specific for their parent construct. Thus, expressing CreX (where the X signifies the inactive dominant-negative mutant) inhibits the activity of Cre but not Dre, while expressing DreX inhibits the activity of Dre and not Cre. By differentially expressing both CreX and DreX, one is able to set independent thresholds for the activity of each enzyme. This type of behavior is useful for therapeutic applications, where a "tumor-hunter" bacteria must carefully calibrate multiple signals in identifying a tumor before it is allowed to initiate production of a toxic chemical.

In another application, the dominant-negative mutant is put under control of a variable strength promoter, while the active recombinase is also under control of a variable strength promoter. As before, when thee construct is tuned so that the initial active:inactive ratio is below the activity threshold, it will not fire. In this case however, since both promoter strengths are changing, the difference in initial promoter strength can be lower (while protein copy number difference is maintained through differences in ribosome binding site strength). This allows the use of native promoter mechanisms to control a circuit in response to a change in cell physiology. This allows access to more "hands-off" circuits, where a cell responds to natural changes in its own environment rather than induced changes (i.e., adding IPTG or arabinose), and to do so in such a way where a strong response can still be generated by use of the active recombinase causing a much stronger promoter to join up to a target DNA.

This approach is also useful in that, in many circuit designs, one can think of a circuit as being made of "cheap" DNA and "expensive" proteins. In other words, it is energetically costly to maintain a protein gradient of activator and repressor pairs, but energetically cheaper to maintain the DNA that encodes those proteins and the DNA that encodes the target DNA elements they act upon. Since recombinases can induce a permanent change in the DNA of a cell without the constant presence of the protein, circuits can be designed that excise both the recombinase and the dominant negative mutant when they are no longer needed, lowering the protein burden on the cell, and only then expressing the next set of necessary proteins. Using this "sliding window" approach allows the circuit to progress towards completion without an exponential increase in protein production to maintain it.

Figure 20:
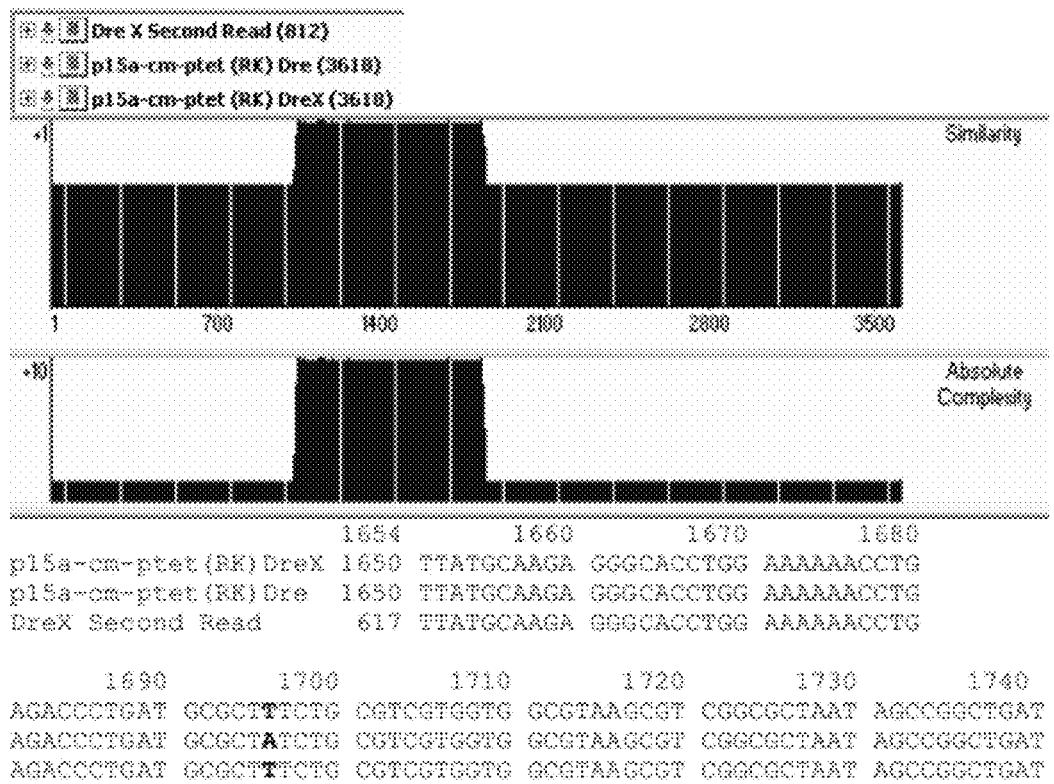
FIG. 20 shows the result of a cross testing method using an active site knockout of Dre (DreX-Y324F). Tyrosine Y324 is annotated as the active site tyrosine for this enzyme. However, after replacing this residue with phenylalanine, as determined in the sequencing result shown, activity of the enzyme is still observed. The nucleotide sequences depicted for "p15a-cm-ptet (RK) DreX" and "DreX Second Read" are SEQ ID NO:19. The nucleotide sequence depicted for "p15a-cm-ptet (RK) Dre" is SEQ ID NO:20.

A knockout of Dre, named DreX(Y324F) is prepared. Tyrosine Y324 is annotated as the active site tyrosine for this enzyme. However, after replacing this residue with phenylalanine, as determined in the sequencing result shown below, one still observes activity of the enzyme using our crosstesting method described herein. See FIG. 20. Activity identical to the native Dre even when DreX(Y324F) is expressed alone. This annotation as the active site residue is incorrect and have moved on to knocking out additional tyrosine residues in Dre, Cre, and FlpSc. This process continues until active site knockouts are identified. One then determines the activation threshold for each pair, determines if the dominant negative pairs are exclusive through crosstesting, and initiates longitudinal studies to determine the fidelity of the thresholds through time.

Example 5

Method of Searching for and Using Orthogonal Site Selective Recombinases

Seven recombinases (Cre, Dre, FlpSc, FlpZb, FlpZf, ΦC31, and Bxb1, where Sc Zb and Zf are different species of yeast) are analyzed for compatibility (ability to act specifically and independently upon their own attachment, att, sites when present in a single cell) in an experimental system (see Tables 4-7). Each is able to produce the desired recombination product using its cognate att sites in our system. Cre is compatible with Dre under some conditions, although some recombination is observed upon sequences flanked by mismatched CreA-DreA att sites (half-sites). This is the only half-site combination that resulted in an excision product. Analysis of the CreA and DreA sites suggest that a functional Holliday junction could be formed, although the identity of the cleavage product has not been determined. Dre and FlpSc are compatible under all conditions, while FlpSc and Cre demonstrated cross-reactivity. The remaining four recombinases show high levels of cross reactivity with non-cognate att sites.

Figure 21:
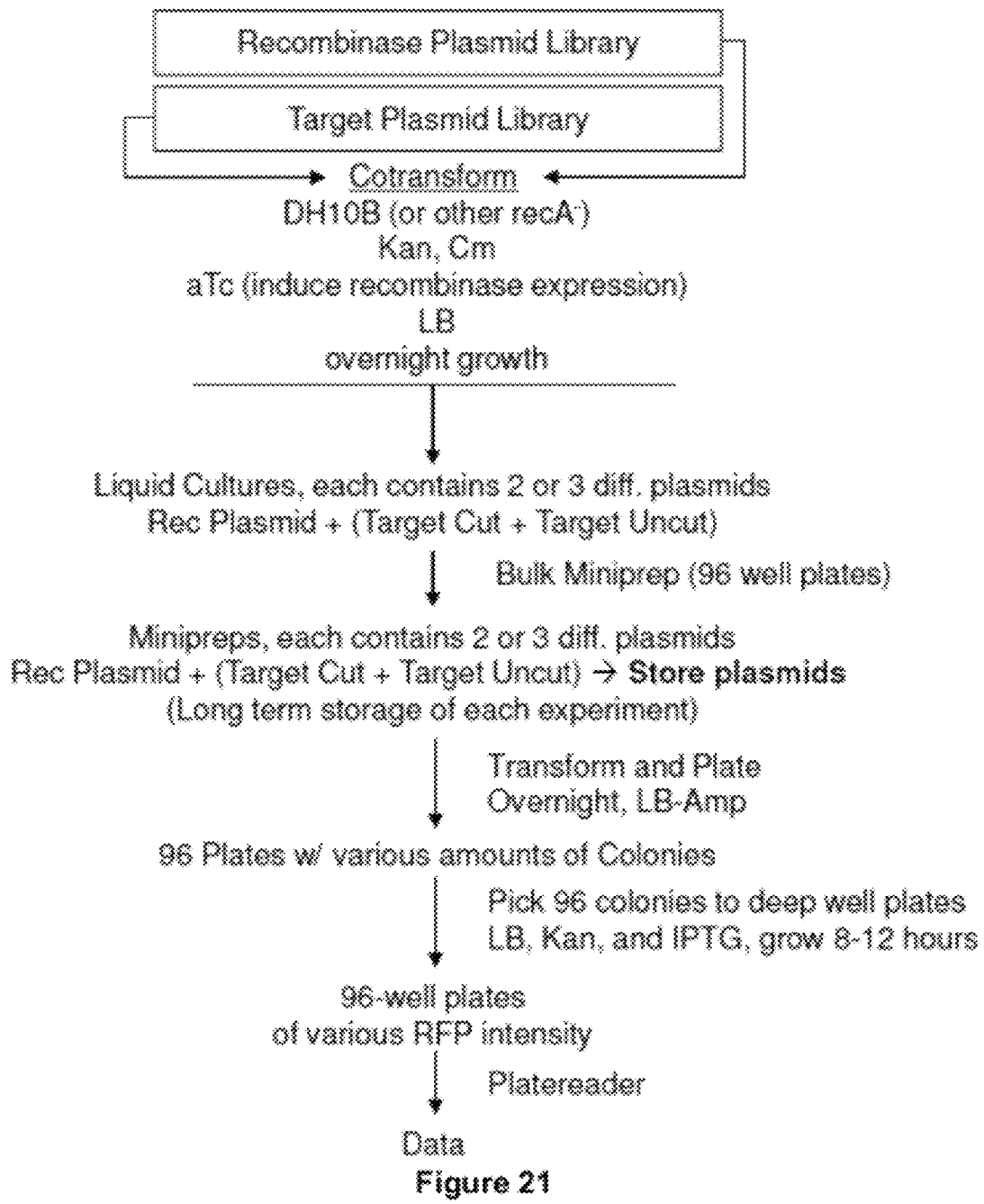
FIG. 21 shows a flowchart for a plate based assay for searching for and using orthogonal site selective recombinases.

The incompatibility between Cre and Dre is easily resolvable by changing the bases of the crossover region to make CreA and DreA an incompatible pair (one that cannot form a holiday junction that permits strand exchange.) The incompatibility between FlpSc and Cre may not be resolvable, but this pairing (and many additional enzymes and binding sites) is currently being testing using a plate based assay that significantly increases our analytical throughput. A flowchart of this process is shown in FIG. 21.

TABLE 4

| | CreA-CreA | DreA-DreA | ScA-ScA | ZbA-ZbA | ZfA-ZfA | ΦC31B-ΦC31B | Bxb1B-Bxb1B |
|---|---|---|---|---|---|---|---|
| Cre | 12/12 | 0/12 | 12/12 | 12/12 | 12/12 | 12/12 | 12/12 |
| Dre | 0/12 | 12/12 | 0/12 | 12/12 | 12/12 | 12/12 | 11/12 |
| FlpSc | 10/12 | 0/11 | 12/12 | 8/8 | 8/8 | 12/12 | 10/11 |
| FlpZb | 12/12 | 12/12 | 12/12 | 12/12 | 12/12 | 12/12 | 12/12 |
| FlpZf | 12/12 | 12/12 | 11/12 | 12/12 | 12/12 | 12/12 | 12/12 |
| ΦC31 | 12/12 | 12/12 | 12/12 | 12/12 | 11/12 | 12/12 | 11/12 |
| Bxb1 | 10/12 | 7/10 | 10/11 | 12/12 | 12/12 | 12/12 | 8/8 |

X/Y - fraction of colonies with observed excision

Bold = desired

Normal = undesired

TABLE 5

Cre and Dre appear to form a highly compatible pair, as do Dre and FlpSc. FlpSc and Cre cross react, and all other combinations show a high incidence of background activity. Only Cre, Dre, and FlpSc are further analyzed for cross-compatability.

| | CreA-CreA | DreA-DreA | ScA-ScA | ZbA-ZbA | ZfA-ZfA | ΦC31B-ΦC31B | Bxb1B-Bxb1B |
|---|---|---|---|---|---|---|---|
| Cre | 12/12 | 0/12 | 12/12 | 12/12 | 12/12 | 12/12 | 12/12 |
| Dre | 0/12 | 12/12 | 0/12 | 12/12 | 12/12 | 12/12 | 11/12 |
| FlpSc | 10/12 | 0/11 | 12/12 | 8/8 | 8/8 | 12/12 | 10/11 |
| FlpZb | 12/12 | 12/12 | 12/12 | 12/12 | 12/12 | 12/12 | 12/12 |
| FlpZf | 12/12 | 12/12 | 11/12 | 12/12 | 12/12 | 12/12 | 12/12 |
| ΦC31 | 12/12 | 12/12 | 12/12 | 12/12 | 11/12 | 12/12 | 11/12 |
| Bxb1 | 10/12 | 7/10 | 10/11 | 12/12 | 12/12 | 12/12 | 8/8 |

X/Y - fraction of colonies with observed excision

Bold = desired

Normal = undesired

TABLE 6

Cross compatability tests are performed by expression one or two enzymes in the presence of either "full" targets (2 identical att sites) or "half" targets (2 non identical att sites). The first 9 boxes are carried over from Table 5.

|  | CreA-CreA | DreA-DreA | ScA-ScA | CreA-DreA- | CreA-ScA | DreA-ScA |
|---|---|---|---|---|---|---|
| Cre | 12/12 | 0/12 | 12/12 | 12/12 | 0/12 | 0/12 |
| Dre | 0/12 | 12/12 | 0/12 | 0/12 | 0/12 | 0/12 |
| FlpSc | 10/12 | 0/11 | 12/12 | 1/12 | 0/10 | 0/11 |
| Cre-Dre | 12/12 | 12/12 | 12/12 | 0/12 | 0/11 | 0/12 |
| Cre-FlpSc | 0/12 | 0/12 | 12/12 | 0/12 | 0/12 | 0/12 |
| Dre-FlpSc | 11/12 | 12/12 | 12/12 | 0/12 | 0/9 | 0/12 |

X/Y - fraction of colonies with observed excision
Bold = desired
Normal = undesired

TABLE 7

The blue shaded boxes show that while Dre does not change it's behavior under any new conditions, Cre alone is able to recombine one CreA site + one DreA site. Further analysis of these att sites suggests a change in the crossover region will resolve this problem.

TABLE 7-continued

Cre and FlpSc continue to show cross-cutting behavior in the presence of Dre. However, neither Cre nor FlpSc show activity on Cre cognate sites when co-expressed (creA-creA column/Cre-FlpSc row).

|  | CreA-CreA | DreA-DreA | ScA-ScA | CreA-DreA- | CreA-ScA | DreA-ScA |
|---|---|---|---|---|---|---|
| Cre | 12/12 | 0/12 | 12/12 | 12/12 | 0/12 | 0/12 |
| Dre | 0/12 | 12/12 | 0/12 | 0/12 | 0/12 | 0/12 |
| FlpSc | 10/12 | 0/11 | 12/12 | 1/12 | 0/10 | 0/11 |
| Cre-Dre | 12/12 | 12/12 | 12/12 | 0/12 | 0/11 | 0/12 |
| Cre-FlpSc | 0/12 | 0/12 | 12/12 | 0/12 | 0/12 | 0/12 |
| Dre-FlpSc | 11/12 | 12/12 | 12/12 | 0/12 | 0/9 | 0/12 |

X/Y - fraction of colonies with observed excision
Bold = desired
Normal = undesired While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

SEQUENCE LISTING

<160> NUMBER OF SEQ ID NOS: 20

<210> SEQ ID NO 1
<211> LENGTH: 34
<212> TYPE: DNA
<213> ORGANISM: Bacteriophage P1

<400> SEQUENCE: 1
ataacttcgt atagcataca ttatacgaag ttat        34

<210> SEQ ID NO 2
<211> LENGTH: 32
<212> TYPE: DNA
<213> ORGANISM: Bacteriophage P1

<400> SEQUENCE: 2
taactttaaa taatgccaat tatttaaagt ta          32

<210> SEQ ID NO 3
<211> LENGTH: 50
<212> TYPE: DNA
<213> ORGANISM: Saccharomyces cerevisiae

<400> SEQUENCE: 3
tttgaagttc ctattccgaa gttcctattc tctagaaagt ataggaactt        50

<210> SEQ ID NO 4
<211> LENGTH: 33
<212> TYPE: DNA
<213> ORGANISM: Artificial sequence
<220> FEATURE:
<223> OTHER INFORMATION: A sequence of interest flanked on the 5' end by

```
      the EcoRI and BglII restriction sites and on the 3' end by the
      BamHI and XhoI restriction sites
<220> FEATURE:
<221> NAME/KEY: misc_feature
<223> OTHER INFORMATION: "nnn" is a sequence of interest that can be any
      nucleotide sequence from any source
<220> FEATURE:
<221> NAME/KEY: misc_feature
<222> LOCATION: (16)..(18)
<223> OTHER INFORMATION: n is a, c, g, or t

<400> SEQUENCE: 4
gaattcaaaa gatctnnngg atccaaactc gag                                    33

<210> SEQ ID NO 5
<211> LENGTH: 15
<212> TYPE: DNA
<213> ORGANISM: Artificial sequence
<220> FEATURE:
<223> OTHER INFORMATION: A sequence of interest flanked on the 5' end by
      the BglII restriction site and on the 3' end by the BamHI
      restriction site
<220> FEATURE:
<221> NAME/KEY: misc_feature
<223> OTHER INFORMATION: "nnn" is a sequence of interest that can be any
      nucleotide sequence from any source
<220> FEATURE:
<221> NAME/KEY: misc_feature
<222> LOCATION: (7)..(9)
<223> OTHER INFORMATION: n is a, c, g, or t

<400> SEQUENCE: 5
agatctnnng gatcc                                                        15

<210> SEQ ID NO 6
<211> LENGTH: 15
<212> TYPE: DNA
<213> ORGANISM: Artificial sequence
<220> FEATURE:
<223> OTHER INFORMATION: A sequence of interest flanked on the 5' end by
      the BglII restriction site and on the 3' end by the BamHI
      restriction site
<220> FEATURE:
<221> NAME/KEY: misc_feature
<223> OTHER INFORMATION: "nnn" is a sequence of interest that can be any
      nucleotide sequence from any source
<220> FEATURE:
<221> NAME/KEY: misc_feature
<222> LOCATION: (7)..(9)
<223> OTHER INFORMATION: n is a, c, g, or t

<400> SEQUENCE: 6
agatctnnng gatcc                                                        15

<210> SEQ ID NO 7
<211> LENGTH: 24
<212> TYPE: DNA
<213> ORGANISM: Artificial sequence
<220> FEATURE:
<223> OTHER INFORMATION: Two sequences of interest flanking a
      BamHI-BglII "scar" and flanked on the 5' end by the BglII
      restriction site and on the 3' end by the BamHI restriction site
<220> FEATURE:
<221> NAME/KEY: misc_feature
<223> OTHER INFORMATION: "nnn" is a sequence of interest that can be any
      nucleotide sequence from any source
<220> FEATURE:
<221> NAME/KEY: misc_feature
<222> LOCATION: (7)..(9)
<223> OTHER INFORMATION: n is a, c, g, or t
<220> FEATURE:
<221> NAME/KEY: misc_feature
<222> LOCATION: (16)..(18)
```

-continued

<223> OTHER INFORMATION: n is a, c, g, or t

<400> SEQUENCE: 7
agatctnnng gatccnnngg atcc                                          24

<210> SEQ ID NO 8
<211> LENGTH: 21
<212> TYPE: DNA
<213> ORGANISM: Artificial sequence
<220> FEATURE:
<223> OTHER INFORMATION: A sequence of interest inserted between an ATG
      start condon and a TAA stop codon and two restriction sites which
      is an exemplary component of the synthetic West Coast BioBrick
      System
<220> FEATURE:
<221> NAME/KEY: misc_feature
<223> OTHER INFORMATION: "nnn" is a sequence of interest that can be any
      nucleotide sequence from any source
<220> FEATURE:
<221> NAME/KEY: misc_feature
<222> LOCATION: (10)..(12)
<223> OTHER INFORMATION: n is a, c, g, or t

<400> SEQUENCE: 8
agatctatgn nntaaggatc c                                             21

<210> SEQ ID NO 9
<211> LENGTH: 21
<212> TYPE: DNA
<213> ORGANISM: Artificial sequence
<220> FEATURE:
<223> OTHER INFORMATION: A sequence of interest inserted between an GTG
      start condon and a TGA stop codon and two restriction sites which
      is an exemplary component of the synthetic West Coast BioBrick
      System
<220> FEATURE:
<221> NAME/KEY: misc_feature
<223> OTHER INFORMATION: "nnn" is a sequence of interest that can be any
      nucleotide sequence from any source
<220> FEATURE:
<221> NAME/KEY: misc_feature
<222> LOCATION: (10)..(12)
<223> OTHER INFORMATION: n is a, c, g, or t

<400> SEQUENCE: 9
agatctgtgn nntgaggatc c                                             21

<210> SEQ ID NO 10
<211> LENGTH: 33
<212> TYPE: DNA
<213> ORGANISM: Artificial sequence
<220> FEATURE:
<223> OTHER INFORMATION: A Type II coding sequence which allows the
      construction of ORF fusions for chimeric and tagged proteins which
      is an exemplary component of the synthetic West Coast BioBrick
      System

<400> SEQUENCE: 10
agatctatga aatttcccgg gaaatttgga tcc                                33

<210> SEQ ID NO 11
<211> LENGTH: 33
<212> TYPE: DNA
<213> ORGANISM: Artificial sequence
<220> FEATURE:
<223> OTHER INFORMATION: A Type III coding sequence which allows the
      construction of ORF fusions for chimeric and tagged proteins which
      is an exemplary component of the synthetic West Coast BioBrick
      System

<400> SEQUENCE: 11

```
agatctcatc atcatcatca tcattaagga tcc                                33
```

<210> SEQ ID NO 12
<211> LENGTH: 33
<212> TYPE: DNA
<213> ORGANISM: Artificial sequence
<220> FEATURE:
<223> OTHER INFORMATION: A Type IV coding sequence which allows the
      construction of ORF fusions for chimeric and tagged proteins which
      is an exemplary component of the synthetic West Coast BioBrick
      System

<400> SEQUENCE: 12

```
agatctaaat ttcccgggaa atttcccgga tcc                                33
```

<210> SEQ ID NO 13
<211> LENGTH: 25
<212> TYPE: DNA
<213> ORGANISM: Artificial sequence
<220> FEATURE:
<223> OTHER INFORMATION: A synthetic ribosome binding sequence between
      two restriction sites which is an exemplary component of the
      synthetic West Coast BioBrick System

<400> SEQUENCE: 13

```
agatctgaaa gaggagaaag gatcc                                         25
```

<210> SEQ ID NO 14
<211> LENGTH: 21
<212> TYPE: DNA
<213> ORGANISM: Artificial sequence
<220> FEATURE:
<223> OTHER INFORMATION: A sequence of interest between a ATG start
      condon and a TAA stop codon and two restriction sites which is an
      exemplary component of the synthetic West Coast BioBrick System
<220> FEATURE:
<221> NAME/KEY: misc_feature
<223> OTHER INFORMATION: "nnn" is a sequence of interest that can be any
      nucleotide sequence from any source
<220> FEATURE:
<221> NAME/KEY: misc_feature
<222> LOCATION: (10)..(12)
<223> OTHER INFORMATION: n is a, c, g, or t

<400> SEQUENCE: 14

```
agatctatgn nntaaggatc c                                             21
```

<210> SEQ ID NO 15
<211> LENGTH: 40
<212> TYPE: DNA
<213> ORGANISM: Artificial sequence
<220> FEATURE:
<223> OTHER INFORMATION: A sequence of interest between a synthetic
      ribosome binding site and ATG start condon and a TAA stop codon
      and two restriction sites which is an exemplary component of the
      synthetic West Coast BioBrick System
<220> FEATURE:
<221> NAME/KEY: misc_feature
<223> OTHER INFORMATION: "nnn" is a sequence of interest that can be any
      nucleotide sequence from any source
<220> FEATURE:
<221> NAME/KEY: misc_feature
<222> LOCATION: (29)..(31)
<223> OTHER INFORMATION: n is a, c, g, or t

<400> SEQUENCE: 15

```
agatctgaaa gaggagaaag gatctatgnn ntaaggatcc                         40
```

<210> SEQ ID NO 16

```
<211> LENGTH: 34
<212> TYPE: DNA
<213> ORGANISM: Artificial sequence
<220> FEATURE:
<223> OTHER INFORMATION: A synthetic promoter sequence flanked on the 5'
      end by the XhoI restriction site and the tet repressor binding
      site and on the 3' end by the BamHI restriction site
<220> FEATURE:
<221> NAME/KEY: misc_feature
<222> LOCATION: (10)..(12)
<223> OTHER INFORMATION: "nnn" is the sequence to which the tet
      repressor binds

<400> SEQUENCE: 16
agatcttccn nntagagata ctgagcacgg atcc                                34

<210> SEQ ID NO 17
<211> LENGTH: 15
<212> TYPE: RNA
<213> ORGANISM: Artificial sequence
<220> FEATURE:
<223> OTHER INFORMATION: A synthetic terminator sequence

<400> SEQUENCE: 17
cuuucugcgu uuaua                                                     15

<210> SEQ ID NO 18
<211> LENGTH: 33
<212> TYPE: DNA
<213> ORGANISM: Escherichia coli
<220> FEATURE:
<223> OTHER INFORMATION: A synthetic terminator sequence flanked on the
      5' end by the XhoI restriction site and the tet repressor binding
      site and on the 3' end by the BamHI restriction site
<220> FEATURE:
<221> NAME/KEY: misc_feature
<222> LOCATION: (10)..(12)
<223> OTHER INFORMATION: "nnn" is the sequence to which the tet
      repressor binds

<400> SEQUENCE: 18
agatctccan nnctttctgc gtttatagga tcc                                 33

<210> SEQ ID NO 19
<211> LENGTH: 90
<212> TYPE: DNA
<213> ORGANISM: Escherichia coli
<220> FEATURE:
<223> OTHER INFORMATION: Dre Y324F knockout
<220> FEATURE:
<221> NAME/KEY: mutation
<222> LOCATION: (46)..(46)
<223> OTHER INFORMATION: Dre Y324F knockout

<400> SEQUENCE: 19
ttatgcaaga gggcacctgg aaaaaactga gaccctgatg cgctttctgc gtcgtggtgg    60
cgtaagcgtc ggcgctaata gccggctgat                                     90

<210> SEQ ID NO 20
<211> LENGTH: 90
<212> TYPE: DNA
<213> ORGANISM: Escherichia coli

<400> SEQUENCE: 20
ttatgcaaga gggcacctgg aaaaaactga gaccctgatg cgctatctgc gtcgtggtgg    60
cgtaagcgtc ggcgctaata gccggctgat                                     90
```

What is claimed is:

1. A recombinant nucleic acid comprising a nucleotide sequence comprising (a) a plurality of constructs comprising a first pair of recombinase recognition sequences which is recognized by a first recombinase, wherein the first pair of recombinase recognition sequences flank a first terminator, and a second pair of recombinase recognition sequences which is recognized by a second recombinase, wherein the second pair of recombinase recognition sequences flank a second terminator, (b) a promoter upstream of the plurality of constructs capable of transcribing the plurality of constructs, wherein each construct independently comprises a nucleotide sequence of interest flanked by a pair of recombinase recognition sequences, wherein each pair of recombinase recognition sequences is recognized by a recombinase that does not cross-react with the recombinase recognition sequences of another construct, and the two recombinase recognition sequences of each pair are oriented in the same direction to each other, and (c) a target gene downstream of the plurality of constructs; wherein the first recombinase and the second recombinase are (i) *Escherichia coli* Cre and Dre, or (ii) Dre and *Saccharomyces cerevisiae* FLP.

2. The recombinant nucleic acid of claim 1 wherein each construct independently further comprises one or more genes encoding a recombinase capable of recognizing the pair of recombinase recognition sequences of the construct.

3. A vector comprising the recombinant nucleic acid of claim 1.

4. An ex vivo host cell comprising the vector of claim 3.

5. The recombinant nucleic acid of claim 1, wherein the target gene encodes an open reading frame (ORF), interference RNA, or antisense RNA.

6. The recombinant nucleic acid of claim 5, wherein the target gene encodes the ORF and the ORF encodes a selective marker, an enzyme, or a polypeptide that cause the death of a host cell.

7. The recombinant nucleic acid of claim 1, wherein the nucleotide sequences of interest are terminators.

8. The recombinant nucleic acid of claim 1, wherein each nucleotide of interest comprises (i) an open reading frame (ORF) of a recombinase which recognizes the pair of recombinase recognition sequences flanking the nucleotide of interest, and (ii) a terminator downstream of the ORF.

9. The recombinant nucleic acid of claim 8, wherein the target gene encodes an open reading frame (ORF) and the ORF encodes a polypeptide that cause the death of a host cell.

10. The recombinant nucleic acid of claim 1, wherein the first pair of recombinase recognition sequences flank a first gene encoding the first recombinase wherein the first gene is upstream of the first terminator, and the second pair of recombinase recognition sequences flank a second gene encoding the second recombinase wherein the second gene is upstream of the second terminator.

* * * * *